(12) United States Patent
Ihara et al.

(10) Patent No.: US 8,288,374 B2
(45) Date of Patent: Oct. 16, 2012

(54) MEDICINAL COMPOSITION CONTAINING BENZO[A]PHENOXAZINE COMPOUND AS THE ACTIVE INGREDIENT FOR PREVENTION OR TREATMENT OF PROTOZOAL DISEASE

(75) Inventors: Masataka Ihara, Tokyo (JP); Jian-Feng Ge, Tokyo (JP); Chika Arai, Tokyo (JP); Nasser Saad Mohamed Ismail, Tokyo (JP); Mei Yang, Tokyo (JP); Isamu Itoh, Tokyo (JP); Reto Brun, Basel (CH)

(73) Assignees: Hoshi University, Tokyo (JP); Synstar Japan Co., Ltd., Kanagawa (JP); Swiss Tropical and Public Health Institute, Basel (CH); FUJIFILM Corporation, Tokyo (JP)

( * ) Notice: Subject to any disclaimer, the term of this patent is extended or adjusted under 35 U.S.C. 154(b) by 130 days.

(21) Appl. No.: 12/921,569

(22) PCT Filed: Mar. 11, 2009

(86) PCT No.: PCT/JP2009/054634
§ 371 (c)(1),
(2), (4) Date: Oct. 12, 2010

(87) PCT Pub. No.: WO2009/113569
PCT Pub. Date: Sep. 17, 2009

(65) Prior Publication Data
US 2011/0021450 A1 Jan. 27, 2011

(30) Foreign Application Priority Data
Mar. 12, 2008 (JP) ................. 2008-062410

(51) Int. Cl.
*C07D 413/12* (2006.01)
*C07D 417/12* (2006.01)
*A61K 31/538* (2006.01)

(52) U.S. Cl. ..................... 514/229.5; 544/99

(58) Field of Classification Search ............... 544/99; 514/229.5
See application file for complete search history.

(56) References Cited

U.S. PATENT DOCUMENTS

| 2,528,862 A | 11/1950 | Crossley |
| 2,528,863 A | 11/1950 | Crossley |
| 2,677,684 A | 5/1954 | Crossley |
| 2008/0015189 A1 | 1/2008 | Hamblin et al. |

FOREIGN PATENT DOCUMENTS

| WO | 2006/087935 A1 | 8/2006 |
| WO | 2006/137258 A1 | 12/2006 |

OTHER PUBLICATIONS

M. L. Crossley, P. F. Dreisbach, C. M. Hofman, R, P. Parker, J. Am. Chem. Soc., 74, 573-578, 1952.
M. L. Crossley, R. J. Turner, C. M. Hofman, P, F. Dreisbach, R. P. Parker, J. Am. Chem. Soc., 74, 578-584, 1952.
M. L. Crossley, C. M. Hofman, P, F. Dreisbach, J. Am. Chem. Soc., 74, 584-586, 1952.
N. Motohashi, Yakugaku Zasshi, 102, 646-650, 1982.
N. Motohashi, Medicinal Research Reviews, 11, 239-294, 1991.
K. Takasu, T. Shimogama, C. Satoh, M. Kaiser, R. Brun, M. Ihara, J. Med. Chem., 50, 2281-2284, 2007.
J. L. Vennerstrom, M. T. Makler, C. K. Angerhofer, J. A. Williams, Antimicrob. Agents Chemother., 39, 2671-2677, 1995.
Suzuki, F., TUmor-specificity and Type of Cell Death Induced by phenoxazines, Anticancer Research, 2007, 27 (6B), p. 4233-4238.
Clapp, R. C., Chemotherapeutic Dyes. IV. Phenoxazines and Benzo[a]phenoxazines, Journal of the American Chemical Society, 1952, 74(8), p. 1989-1993.
Vennerstrom, J.L., Antimalarial Dyes Revisited: Xanthens, Azines, Oxazines, and Thiazines, Antimicrobial Agents and Chemotherapy, 1995, 39(12), p. 2671-2677.
Akilov, O. E., The Role of Photosensitizer Molecular Change and Structure on the Efficacy of Photodynamic Therapy against Leishmania Parasites, Chemistry & Biology, 2006, 13(8), p. 839-847.

*Primary Examiner* — Kahsay T Habte
(74) *Attorney, Agent, or Firm* — SOLARIS Intellectual Property Group, PLLC

(57) ABSTRACT

Provided is a medicinal composition, in particular, a medicinal composition for treatment and/or prevention which has a high therapeutic effect on infection with a parasitic protozoa and a selective toxicity thereto and exhibits a life-prolonging effect and so on. A medicinal composition which contains as the active ingredient a benzo[a]phenoxazine compound represented by General formula (1) or a salt compound of the same, in particular, an agent for treating and/or preventing infection with a protozoa such as malaria, leishmaniasis, African trypanosomiasis, Chagas disease, toxoplasmosis, lymphatic filariasis, babesiosis or coccidium disease; and a novel compound which is contained therein as the active ingredient.

17 Claims, No Drawings

MEDICINAL COMPOSITION CONTAINING BENZO[A]PHENOXAZINE COMPOUND AS THE ACTIVE INGREDIENT FOR PREVENTION OR TREATMENT OF PROTOZOAL DISEASE

TECHNICAL FIELD

The present invention relates to a medicinal composition containing as an active ingredient a benzo[a]phenoxazine compound for prevention or treatment and to a benzo[a]phenoxanzine compound. The medicinal composition of the present invention is useful for treatment and/or treatment of diseases related to parasitic infections, especially for example, malaria including drug-resistant malaria, leishmaniasis, trypanosomiasis including African Trypanosomiasis and Chagas disease, toxoplasmosis and cryptosporidiosis.

BACKGROUND ART

Even now, parasitic protozoan infections are widely known mainly around tropical or subtropical regions, and can be exemplified by malaria, leishmaniasis, African trypanosomiasis (African sleeping sickness), American trypanosomiasis (Chags disease), lymphatic filariasis, babesiosis, cryptosporidiosis and toxoplasmosis. These infections can be classified into those infecting only humans, and parasitic zoonosis also infecting domestic animals or small animals, both leading to significant economic and social loss.

Among these diseases, there are some diseases which do not have a therapeutic agent showing a sufficient effect, or some diseases which have problems such as emergence and diffusion of drug-resistant protozoa, or side effects of therapeutic agents. Therefore, an effective agent is desired. Further, since these diseases include diseases which cause serious symptoms with which patients cannot have a normal social life, diseases which force patients to be in a bedridden state in which nursing care is necessary, and diseases which lead to development of lethal symptoms, rapid development of a chemotherapeutic agent is an absolute necessity. However, there are no vaccines showing effectiveness against these diseases at present, and their future development is also said to be difficult. Under such circumstances, development of a chemotherapeutic agent which can be taken orally or by injection, or administered in a similar way thereto is strongly desired.

Masataka Ihara, one of the present inventors, and his collaborators have carried out research and development of a medicinal composition for prevention or therapy of a protozoal disease, containing as an active ingredient a phenoxanizium compound (Patent Document 1); and a medicinal composition for prevention or therapy of a protozoal disease, containing as an active ingredient an azarhodacyanine compound (Patent Document 2).

A number of benzo[a]phenoxzines and benzo[a]phenoxazonium compounds 1 which are salts thereof with acids have been synthesized so far, and reported to have antitumor activities (Non-patent Documents 1 to 5). On the other hand, in terms of reported examples of inhibitory activities on the growth of protozoans which cause tropical diseases such as malaria, there are cases wherein $R^3$ in General formula (1) is a hydrogen atom or an ethyl group, but their in vitro and in vivo activities are low (Non-patent Documents 6 and 7).

Patent Document 1: International Publication WO2006/087935
Patent Document 2: International Publication WO2006/137258

Non-patent Document 1: M. L. Crossley, P. F. Dreisbach, C. M. Hofman, R, P. Parker, J. Am. Chem. Soc., 74, 573-578, 1952

Non-patent Document 2: M. L. Crossley, R. J. Turner, C. M. Hofman, P, F. Dreisbach, R. P. Parker, J. Am. Chem. Soc., 74, 578-584, 1952

Non-patent Document 3: M. L. Crossley, C. M. Hofman, P, F. Dreisbach, J. Am. Chem. Soc., 74, 584-586, 1952

Non-patent Document 4: N. Motohashi, Yakugaku Zasshi, 102, 646-650, 1982

Non-patent Document 5: N. Motohashi, Medicinal Research Reviews, 11, 239-294, 1991

Non-patent Document 6: K. Takasu, T. Shimogama, C. Satoh, M. Kaiser, R. Brun, M. Ihara, J. Med. Chem., 50, 2281-2284, 2007

Non-patent Document 7: J. L. Vennerstrom, M. T. Makler, C. K. Angerhofer, J.

A. Williams, Antimicrob. Agents Chemother., 39, 2671-2677, 1995

DISCLOSURE OF THE INVENTION

Problems to be Solved by the Invention

The present invention aims to provide a novel medicinal composition for prevention and/or treatment having both excellent therapeutic effect and selective toxicity for a parasitic protozoal disease, especially, a medicinal composition for prevention and treatment which has low toxicity in a living body suffering from a parasitic protozoal disease and exhibits a significant therapeutic effect when it is administered.

Means for Solving the Problems

The present inventors tested effects of various compounds on the growth of protozoans responsible for diseases, and evaluated their cytotoxicities to mammalian cells, which are useful as indices of side effects. Further, among the compounds selected in the above tests, compounds which show suppressing effects of not less than 50% on the growth of malaria parasites were searched by using mice infected with malaria as host models and administering each compound to the mice in various amounts and by various administration modes to evaluate the therapeutic effect of the compound on malaria. As a result, the present inventors first discovered that medicinal compositions each comprising, as an active ingredient, a benzo[a]phenoxzine compound represented by the following General formula 1 or a salt thereof have excellent prophylactic or therapeutic effect for protozoal diseases, thereby completing the present invention based on these findings.

That is, the present invention includes the following modes.

1. A medicinal composition for prevention or treatment of a protozoal disease, the medicinal composition comprising, as an active ingredient, a benzo[a]phenoxazine compound represented by following General formula (1), or a salt thereof:

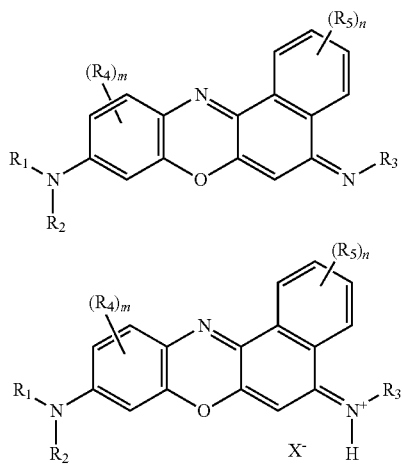

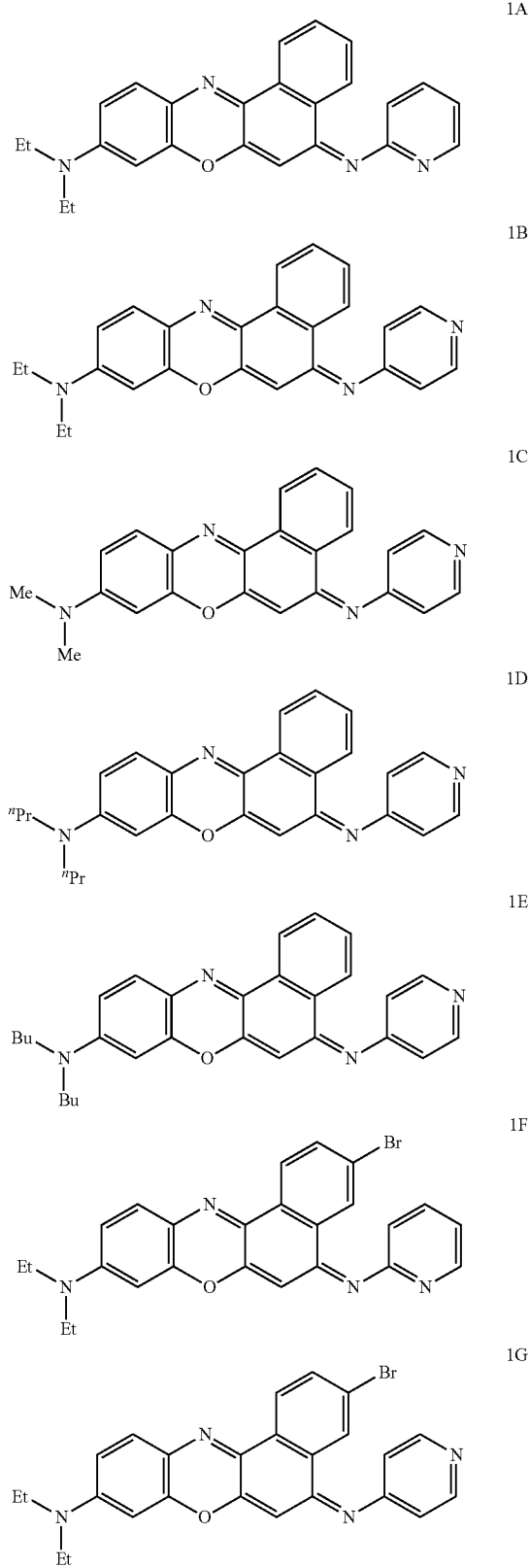

wherein, in General formula (1), $R^1$ and $R^2$ each independently represents a hydrogen atom, a substituted or unsubstituted alkyl group, alkenyl group, aryl group or heterocyclic residue, or $R^1$ and $R^2$ are condensed to form a ring; $R^3$ represents a substituted or unsubstituted alkenyl group, aryl group or heterocyclic residue; $R^4$ and $R^5$ each independently represents a halogen atom, a substituted or unsubstituted alkyl group, alkenyl group, aryl group, alkoxy group, alkylthio group or amino group; m represents an integer of from 0 to 3; n represents an integer of from 0 to 5; and $X^-$ represents an anion.

2. The medicinal composition according to claim 1, wherein, in General formula (I), $R^1$ and $R^2$ each independently represents a hydrogen atom, an alkyl group having 1 to 8 carbon atoms, an alkenyl group having 3 to 8 carbon atoms, an aryl group having 6 to 10 carbon atoms or a heterocyclic residue having 1 to 10 carbon atoms; $R^3$ represents an alkenyl group having 3 to 8 carbon atoms, an aryl group having 6 to 10 carbon atoms or a heterocyclic residue having 1 to 10 carbon atoms; $R^4$ and $R^5$ each independently represents a halogen atom or an alkyl group having 1 to 8 carbon atoms; m and n each independently represents 0 or 1; and the anion represented by $X^-$ is a chlorine atom, a bromine atom, a nitrate ion, a sulfate ion, a p-toluenesulfonate ion or an oxalate ion.

3. The medicinal composition according to 1 or 2, wherein, in General formula (1), $R^1$ and $R^2$ each independently represents a methyl group, an ethyl group, a propyl group, a 2-hydroxyethyl group or a 2-methanesulfonamidoethyl group; and $R^3$ represents a heterocyclic residue.

4. The medicinal composition according to 3, wherein $R^3$ represents a pyridyl group, a pyrimidyl group, an imidazolyl group, a tetrazolyl group or a thiazolyl group.

5. The medicinal composition according to any one of 1 to 4, wherein $R^4$ represents a fluorine atom, a chlorine atom, a methoxy group, an ethoxy group or a methyl group.

6. The medicinal composition according to 5, wherein positions of substitution of $R^4$ include an 11-position.

7. The medicinal composition according to any one of 1 to 6, wherein $R^5$ represents a fluorine atom, a chlorine atom or a methyl group.

8. The medicinal composition according to 7, wherein positions of substitution of $R^5$ include a 3-position.

9. A medicinal composition for prevention or treatment of a protozoal disease, the medicinal composition comprising, as an active ingredient, a compound represented by any one of the following structural formula 1A to 1T and 1a to 1 h, or a salt thereof.

1H
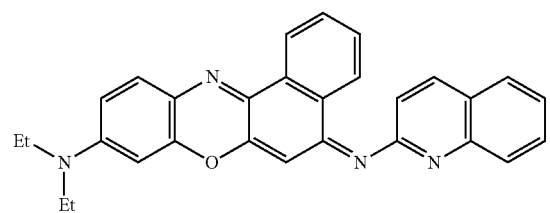
1I
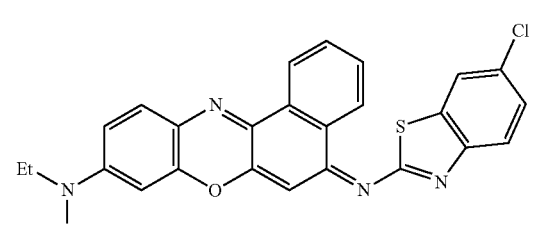
1J
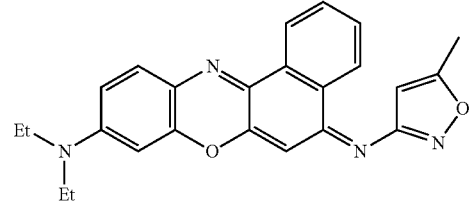
1K
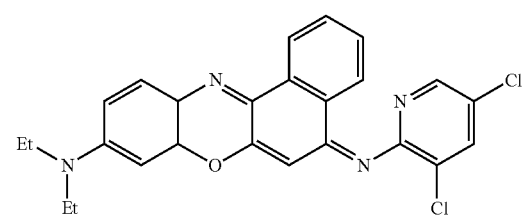
1L
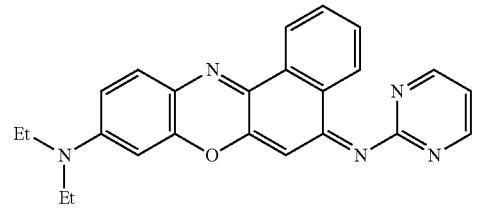
1M
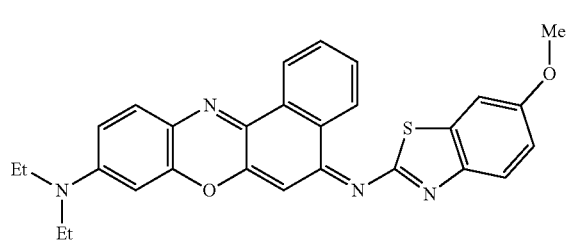
1N
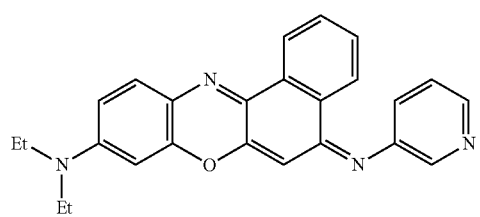
1O
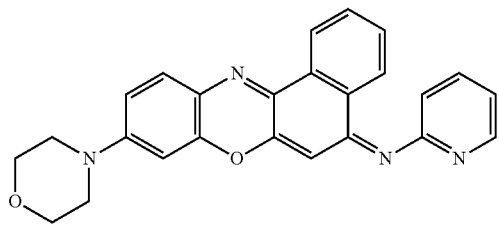
1P
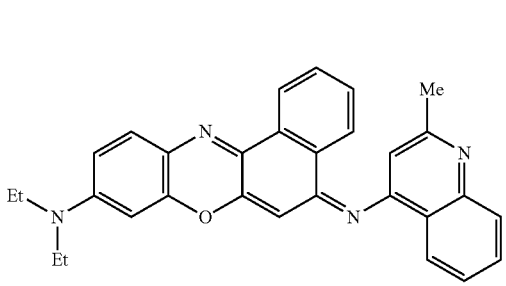
1Q
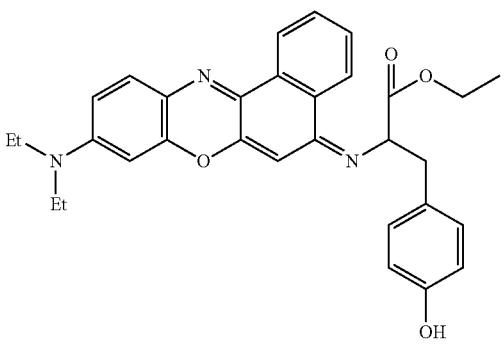
1R
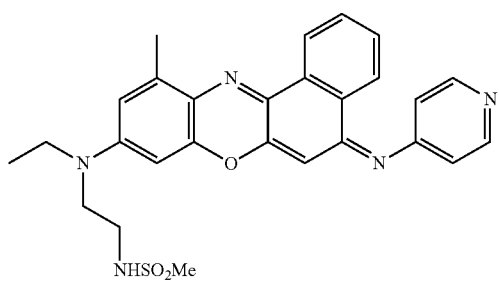
1S
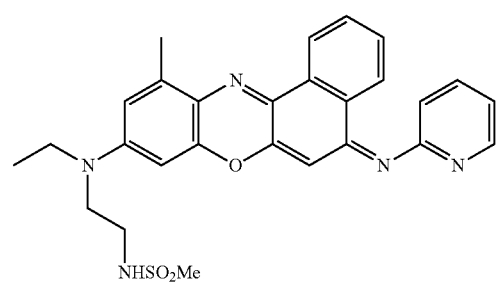

1T 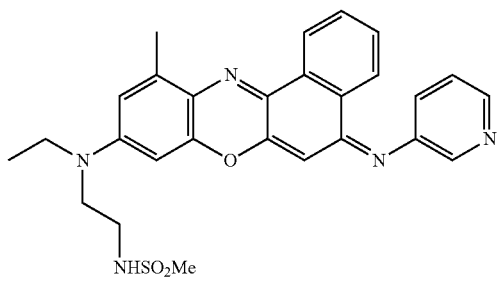

1a 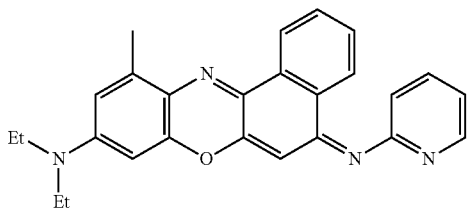

1b 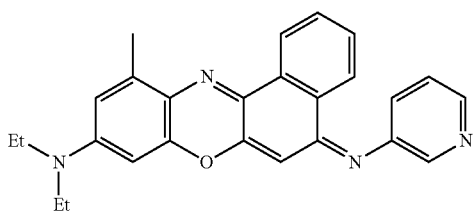

1c 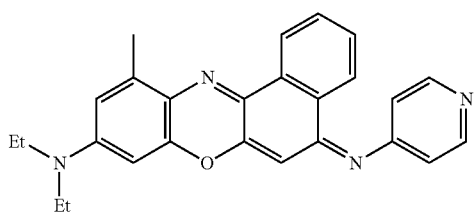

1d 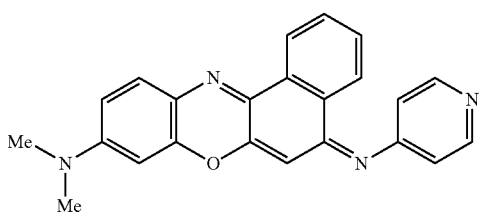

1e 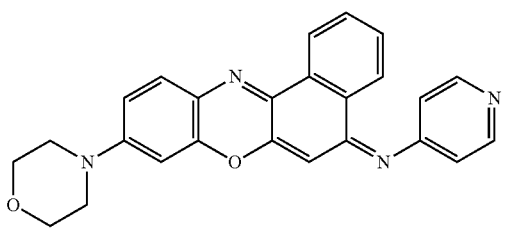

1f 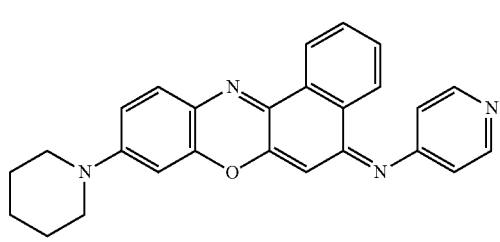

1g 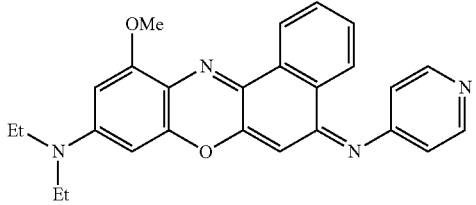

1h 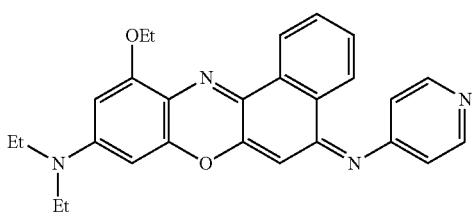

10. The medicinal composition according to any one of 1 to 9, wherein the protozoal disease is malariosis, leishmaniasis, African sleeping sickness, Chagas disease, toxoplasmosis, lymphatic filariasis, babesiosis or coccidiosis.

11. The medicinal composition according to 10, wherein the protozoal disease is malariosis, leishmaniasis, African sleeping sickness or Chagas disease.

12. A compound represented by any one of the above structural formula 1A to 1T and 1a to 1h.

Effect of the Invention

The benzo[a]phenoxazine compound or a salt thereof contained as an active ingredient in the medicinal composition of the present invention exhibits a growth inhibitory effect on a parasitic protozoal disease even by its administration at a low dose, and even in cases where it is administered at a higher dose than that at which an inhibitory effect on a parasitic protozoan is exhibited, mammalian cells are not injured (that is, it has a high selective toxicity coefficient). Further, in in vivo therapeutic tests using mice infected with malaria, the compounds were confirmed to show significantly higher cure rates and significantly higher survival advantages compared to conventionally known compounds. Further, since the compounds have extremely lower acute toxicities, they were confirmed to be effective also as therapeutic agents for malaria and the like having less side effects.

BEST MODE FOR CARRYING OUT THE INVENTION

The medicinal composition of the present invention will now be described in detail. Hereinafter, when a compound is simply described as "compound of the present invention", it means any compound of the present invention represented by General formula (1). Particular examples and preferred examples of each portion of the compound of the present invention will now be described, but the scope of the present invention is not restricted thereto.

Specific examples of the compound of the present invention represented by General formula (1) include those wherein $R^1$ and $R^2$ each independently represents a hydrogen atom, an alkyl group having 1 to 8 carbon atoms, an alkenyl group having 3 to 8 carbon atoms, an aryl group having 6 to 10 carbon atoms or a heterocyclic residue having 1 to 10 carbon atoms; $R^3$ represents an alkenyl group having 3 to 8 carbon atoms, an aryl group having 6 to 10 carbon atoms or a heterocyclic residue having 1 to 10 carbon atoms; and $R^1$ and $R^2$ may be condensed to form a ring. Preferred examples of the alkyl group having 1 to 8 carbon atoms include a methyl group, an ethyl group, a propyl group, a butyl group, a pentyl group, a hexyl group, a cyclohexyl group and an octyl group. Preferred examples of their substituents include a fluorine atom, a chlorine atom, a hydroxy group, an alkoxy group, an amino group, an oxycarbonyl group, a carboxy group, a carbonamide group and a sulfonamide group. Preferred examples of the alkenyl group having 3 to 8 carbon atoms include a vinyl group, an allyl group, a butenyl group and an octenyl group, and examples of substituents thereof include a fluorine atom and a chlorine atom. Preferred examples of the aryl group having 6 to 10 carbon atoms include a phenyl group and a naphthyl group, and examples of substituents thereof include a fluorine atom, a chlorine atom, a methyl group, an ethyl group, a propyl group, a hydroxy group, an alkoxy group, an amino group and a carboxy group. Examples of the heterocyclic residue having 1 to 10 carbon atoms include a pyridyl group, a pyrimidyl group, a triazyl group, a pyridazyl group, an imidazolyl group, a triazolyl group, a tetrazolyl group, a thiazolyl group and an oxazolyl group, and preferred examples of substituents thereof include a fluorine atom, a chlorine atom, a methyl group, an ethyl group, a propyl group, a hydroxy group, an alkoxy group, an amino group, a carboxy group and a pyridyl group. m and n each preferably represent 0 or 1. Preferred examples of the anion represented by X include a chlorine atom, a bromine atom, a nitrate ion, a sulfate ion, a p-toluenesulfonate ion and an oxalate ion, and it especially preferably represents a chloride ion. $R^4$ preferably represents a halogen atom, an alkoxy group or an alkyl group having 1 to 8 carbon atoms such as a methyl group, and is especially preferably a fluorine atom, a chlorine atom, a methoxy group, an ethoxy group or a methyl group, and its position of substitution is the 11-position. $R^5$ especially preferably represents a fluorine atom, a chlorine atom or a methyl group, and its position of substitution is especially preferably the 3-position. Examples of substituents of $R^4$ and $R^5$ include a fluorine atom, a hydroxy group and an alkoxy group.

$R^1$ and $R^2$ especially preferably represent a methyl group, an ethyl group, a propyl group, a 2-hydroxyethyl group or a 2-methanesulfonamidoethyl group. $R^3$ preferably represents a heterocyclic residue; more preferably represents a pyridyl group, a pyrimidyl group, an imidazolyl group, a tetrazolyl group or a thiazolyl group; and especially preferably represents a pyridyl group or an imidazolyl group.

Among the compounds included in the compounds of the present invention represented by the above General formula (1), all the compounds represented by the structural formula 1A to 1T below and salts thereof are especially preferred examples of active ingredients for the medicinal composition of the present invention. Further, these compounds themselves are novel substances, and therefore the present invention also relates to these novel compounds themselves.

The medicinal composition containing the above-described compound of the present invention may be used effectively for preventing or treating various types of diseases caused by parasitic protozoan infections, including malaria, African trypanosomiasis (alias Afican sleeping sickness), American trypanosomiasis (alias Chagas disease), leishmaniasis, babesiosis, lymphatic filariasis, toxoplasmosis (opportunistic infection disease including AIDS) and cryptosporidiosis (tropical diarrhea).

In the medicinal composition of the present invention, 1 or more compounds of the present invention may be contained as active ingredients, and further, as required, the medicinal composition of the present invention may be used in combination with other arbitrary therapeutic agents known to those skilled in the art, including agents for protozoan infections which have been conventionally used. Suitable examples of anti-protozoan infection agents which are used conventionally include: chloroquine, mefloquine, artemisinin, atavaquone, and pyrimethamine (treating agents for malaria infection); suramin, pentamidine, melarsoprol and ascofuranone (treating agents for African trypanosomiasis); benznidazole (treating agents for Chagas disease); pentostam, Amphotericin B, miltefosine and fluconazole (treating agents for leishmaniasis).

Suitable examples of medicinal carriers or diluents that can be used in combination with the compounds shown by general formulae (1) of the present invention include the following: sodium chloride; magnesium chloride; zinc chloride; glucose; saccharose; lactose; ethyl alcohol; glycerol; mannitol; sorbitol; pentaerythritol; diethylene glycol; propylene glycol, dipropylene glycol, polyethylene glycol 400, other polyethylene glycol; mono-, di- and tri-glyceride of fatty acids including trilaurate glyceryl and distearate glyceryl; pectin; starch; arginine acid; xylose; talc; *lycopodium*; olive oil; oil and fat including peanut oil, castor oil, corn oil, safflower oil, wheat germ oil, sesame oil, cotton seed oil, sunflower oil and oleum morrhuae; gelatin; lecithin; silica; cellulose; cellulose derivatives including methylhydroxypropyl cellulose, methyl cellulose and hydroxyethyl cellulose; salts of fatty acids with 12 to 22 carbon atoms including calcium stearate, calcium laureate, magnesium oleate, calcium palminate, calcium behanate and magnesium stearate; cyclodextrins (for example, α-cyclodextrin, β-cyclodextrin, γ-cyclodextrin, hydroxyethyl-β-cyclodextrin, hydroxypropyl-β-cyclodextrin, dihydroxypropyl-β-cyclodextrin, carboxymethylethyl-β-cyclodextrin, cycloawaodorin, and dimethyl-β-cyclodextrin, etc.); emulsifier (for example, ester of saturated and unsaturated fatty acids with 2 to 22, particularly 10 to 18 carbon atoms, with monovalent aliphatic alcohol or polyvalent alcohol with 1 to 20 carbon atoms including glycol, glycerine, diethylene glycol, pentaerythritol, ethyl alcohol and butyl alcohol, octadecyl alcohol); and silicone such as dimethylpolysiloxane. Further, arbitrary additional carriers conventionally used for medical composition and known to those skilled in the art can be also used for the medical composition of the present invention.

Pharmaceutically effective dose and administration method or administration means of the compounds of the present invention can be arbitrarily selected by those in the art depending on types of parasitic protozoa being the cause of the infection, habitats of protozoa, seriousness of diseases, treatment starategies, age, body weight, sex and general health conditions of the patient, and (genetic) racial background of the patient. Generally, the dosage of the present invention is 1 to 10,000 mg/day/70 Kg of body weight, more generally 50 to 2000 mg/day/70 kg of body weight.

The medicinal compositions of the present invention may be formed into arbitrary forms known to those skilled in the art, depending on their administration methods, administration routes and/or the like. These may be administered by appropriate methods. Their examples include ones having the forms of a liquid, tablet and colloid, and in cases where it is a liquid, examples of the method of its administration include intravenous, intraperitoneal and subcutaneous injection of the composition dissolved in aqueous 5% glucose solution or accompanied by the above carrier or diluent. In the case of a tablet, examples of the method of its administration include oral administration, and in the case of a colloid, examples thereof include application to the skin. The compound represented by the above General formula (1) may be contained in an appropriate amount depending on the purpose of use, subject, form and the like of the medicinal composition of the present invention, and is usually contained in an amount of about 1 mg to 10,000 mg, preferably 10 mg to 3,000 mg.

EXAMPLES

To describe the present invention in detail, synthesis examples of the compound of the present invention represented by any of the structural formula 1A to 1 T, and effectiveness of these compounds will now be shown. That is, in order to demonstrate the effectiveness of these compounds and medicinal compositions comprising them, evaluations were carried out by in vitro screening tests for their inhibitory activities on the growth of malaria parasites, *leishmania* parasites, African *trypanosoma* parasites and American *trypanosoma* parasites, and in vivo tests for their therapeutic effects using mice infected with malaria. However, the technical scope of the present invention is not restricted to these Examples.

[Synthesis of Benzo[a]phenoxazine Compound]

In the reaction formulae below, benzo[a]phenoxazine compounds represented by General formula 1 and salts thereof were obtained by the process wherein a 4-nitrosoaniline derivative represented by General formula 3 or a p-phenylenediamines represented by General formula 5 was allowed to react with a 2-naphthol derivative represented by General formula 4 in the presence of an oxidizing agent such as $HNO_3$ to obtain 2, which was then allowed to react in ethanol in the presence of a primary amine and an oxidizing agent containing oxygen, to obtain benzo[a]phenoxazine 1 in the form of a free base as a stable substance. Their structures were determined by $^1H$ and $^{13}C$ NMR, IR, UV, mass spectrometry and elementary analysis. These can be purified also as hydrochloric acid salts. All of 1A to 1T are novel compounds.

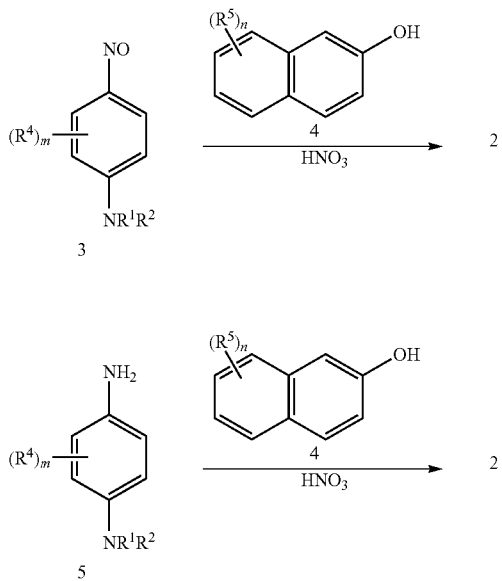

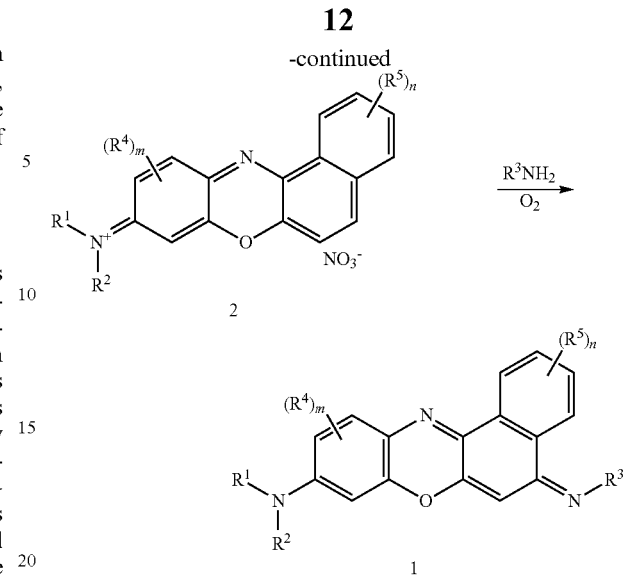

[Examples of Benzo[a]phenoxazine Compounds of Present Invention]

Synthesis of Benzo[a]phenoxazines 1A to 1T

Benzo[a]phenoxazinium nitrate 2 (Non-patent Document 3) (1 mmol) was dissolved in ethanol (5 mL), and an amine (3 mmol) corresponding thereto was added to the resulting solution at one time with stirring, followed by heating the resulting mixture to reflux overnight and then stirring it at room temperature for 1 day. After evaporation of the solvent, the resulting residue was purified twice by silica gel chromatography. As the eluent, $CHCl_3$:MeOH (10:1, v/v) was first used, followed by using $CHCl_3$:MeOH (10:0.3, v/v). After evaporation of the solvent, the resulting product was washed with AcOEt and then $Et_2O$, to obtain benzo[a]phenoxazines 1A to T.

N,N-Diethyl-5-(pyridin-2-ylimino)-5H-benzo[a]phenoxazin-9-amine (1A)

Yield 55%, mp 169-170° C.; IR ν (neat, $cm^{-1}$): 2975, 1645, 1590, 1580, 1490, 1455, 1270, 1220, 1110; UV-vis ($CHCl_3$): λ (nm) (log ε/L $mol^{-1}cm^{-1}$): 532 (4.57); $^1H$ NMR (400 MHz, $CDCl_3$) δ ppm 1.20 (t, J=7.1 Hz, 6H), 3.39 (q, J=7.1 Hz, 4H), 6.27 (d, J=2.7 Hz, 1H), 6.43 (s, 1H), 6.54 (dd, J=9.0, 2.7 Hz, 1H), 6.99-7.03 (m, 2H), 7.49 (d, J=9.0 Hz, 1H), 7.60-7.72 (m, 3H), 8.50-8.51 (m, 1H), 8.60-8.64 (m, 2H); $^{13}C$ NMR (101 MHz, $CDCl_3$) δ ppm 12.6, 44.9, 96.3, 99.1, 108.6, 117.0, 118.6, 123.7, 124.7, 125.3, 129.8, 130.1, 130.3, 131.6, 132.8, 137.6, 141.9, 146.6, 148.9, 149.0, 149.9, 157.9, 163.8; MS ($EI^+$): m/z: 394 [M×]$^+$; HRMS ($EI^+$) 394.1793 [M×]$^+$, found 394.1767. Anal. Calcd. For $C_{25}H_{22}N_4O×0.75H_2O$: C, 73.60; H, 5.81; N, 13.73. Found: C, 73.68; H, 5.57; N, 13.43.

N,N-Diethyl-5-(pyridin-4-ylimino)-5H-benzo[a]phenoxazin-9-amine (1B)

Yield 38%, mp 247-248° C.; IR ν (neat, $cm^{-1}$): 2975, 1640, 1595, 1575, 1490, 1455, 1270, 1220, 1110; UV-vis ($CHCl_3$): λ (nm) (log ε/L $mol^{-1}cm^{-1}$): 713 (4.48), 537 (4.49); $^1H$ NMR (400 MHz, $CDCl_3$) δ ppm 1.21 (t, J=7.1 Hz, 6H), 3.41 (q, J=7.1 Hz, 4H), 6.13 (s, 1H), 6.29 (d, J=2.7 Hz, 1H), 6.57 (dd, J=9.0, 2.7 Hz, 1H), 6.85-6.86 (m, 2H), 7.50 (d, J=9.0 Hz, 1H), 7.61-7.69 (m, 2H), 8.50-8.52 (m, 2H), 8.54 (dd, J=7.9, 1.4 Hz, 1H), 8.62 (dd, J=7.9, 1.3 Hz, 1H); $^{13}C$ NMR (101 MHz, $CDCl_3$) δ ppm 12.6, 44.9, 96.3, 97.7, 108.8, 116.0, 123.9, 124.7, 125.1, 129.9, 130.3, 130.5, 131.6, 132.2, 141.5, 146.6, 149.1, 150.0, 150.4, 156.8, 159.4; MS (EI$^+$): m/z: 394 [M×]$^+$; HRMS (EI$^+$) 394.1793 [M×]$^+$, found 394.1807. Anal. Calcd. For $C_{25}H_{22}N_4O \times 0.25H_2O$: C, 75.26; H, 5.68; N, 14.04. Found: C, 75.31; H, 5.10; N, 13.88.

1B.HCl mp>300; IR ν (neat, cm$^{-1}$): 2920, 2850, 1638, 1579, 1518, 1318, 1251, 1162, 1077; UV-vis (EtOH): λ (nm) (log ε/L mol$^{-1}$cm$^{-1}$): 602 (4.64), 213 (4.63); $^1$H NMR (400 MHz, CD$_3$OD) δ ppm 1.47 (t, J=7.2 Hz, 6H), 4.02 (dd, J=20.5, 7.1 Hz, 4H), 7.38 (d, J=2.6 Hz, 1H), 7.60 (d, J=7.5 Hz, 2H), 7.93-7.87 (m, 1H), 7.97 (dd, J=10.0, 2.6 Hz, 1H), 8.02 (d, J=7.3 Hz, 1H), 8.05 (s, 1H), 8.15 (d, J=10.0 Hz, 1H), 8.34 (d, J=8.4 Hz, 1H), 8.46 (d, J=7.5 Hz, 2H), 9.17 (d, J=8.1 Hz, 1H); MS (ESI$^+$): m/z: 395.2 [M-Cl]$^+$; Anal Calcd. For $C_{25}H_{23}ClN_4O \times 2.5H_2O$: C, 63.09; H, 5.93; N, 11.77. Found: C, 62.66; H, 5.42; N, 11.57.

N,N-Dimethyl-5-(pyridin-4-ylimino)-5H-benzo[a]phenoxazin-9-amine (1C)

Yield 44%, mp 217-218° C.; IR ν (neat, cm$^{-1}$): 2954, 2887, 1628, 1592, 1577, 1447, 1442, 1359, 1200, 1111, 1002, 746; UV-vis (CHCl$_3$): λ (nm) (log ε/L mol$^{-1}$cm$^{-1}$): 546 (4.42), 236 (4.21); $^1$H NMR (400 MHz, CDCl$_3$) δ ppm 3.07 (s, 6H), 6.14 (s, 1H), 6.33 (d, J=2.9 Hz, 1H), 6.61 (dd, J=9.0, 2.7 Hz, 1H), 6.85-6.87 (m, 2H), 7.48 (d, J=9.0 Hz, 1H), 7.53-7.55 (m, 2H), 7.66-7.7 (m, 2H), 8.53 (dd, J=7.9, 1.4 Hz, 1H), 8.64 (dd, J=7.9, 1.3 Hz, 1H); $^{13}$C NMR (101 MHz, CDCl$_3$) δ ppm 40.3, 96.9, 97.9, 109.1, 112.9, 116.9, 123.9, 125.1, 129.2, 130.1, 130.4, 131.5, 132.2, 142.1, 146.2, 149.08, 152.2, 156.8, 159:4; MS (EI$^+$): m/z: 367.1 [M+1]$^+$; HRMS (EI$^+$) 366.1478 [M×]$^+$, found 366.1480.

N,N-Dipropyl-5-(pyridin-4-ylimino)-5H-benzo[a]phenoxazin-9-amine (1 D)

Yield 39%, mp 215-216° C.; IR ν (neat, cm$^{-1}$): 2962, 2876, 1635, 1580, 1547, 1483, 1458, 1361, 1238, 1112, 772; UV-vis (CHCl$_3$): λ (nm) (log ε/L mol$^{-1}$cm$^{-1}$): 716 (4.97), 550 (5); $^1$H NMR (400 MHz, CDCl$_3$) δ ppm 1.051 (t, J=7.2 Hz, 6H), 1.57 (m, 4H), 3.5 (t, J=7.1 Hz, 4H), 6.31 (s, 1H), 6.6 (d, J=2.6 Hz, 1H), 6.99 (dd, J=8.9, 2.7 Hz, 1H), 7.14-7.16 (m, 2H) 7.71-7.77 (m, 2H), 7.8 (d, J=9.0 Hz, 1H), 8.45 (dd, J=7.9, 1.4 Hz, 1H), 8.72-8.76 (m, 2H), 8.9 (dd, J=7.9, 1.3 Hz, 1H); $^{13}$C NMR (101 MHz, CDCl$_3$) δ ppm 11.3, 20.5, 53.1, 96.4, 97.2, 109.6, 116.8, 123.9, 125.1, 125.3, 129.9, 130.6, 130.7, 131.7, 132.4, 140.7, 146.6, 149.7, 150.9, 151.7, 152.2, 157.4; MS (EI$^+$): m/z: 422 [M×+1]$^+$; HRMS (E$^+$) 422.2106 [M×]$^+$, found 422.2128.

N,N-Dibutyl-5-(pyridin-4-ylimino)-5H-benzo[a]phenoxazin-9-amine (1D)

Yield 25%, mp 188-189° C.; IR ν (neat, cm$^{-1}$): 2950, 2872, 1626, 1581, 1514, 1457, 1365, 1324, 1285, 1218, 772; UV-vis (CHCl$_3$): λ (nm) (log ε/L mol$^{-1}$cm$^{-1}$): 545 (4.06), 222 (3.92); $^1$H NMR (400 MHz, CDCl$_3$) δ ppm 0.97 (t, J=7.3 Hz, 6H), 1.37 (m, 4H), 1.6 (m, 4H), 3.3 (t, J=7.2 Hz, 4H), 6.13 (s, 1H), 6.27 (d, J=2.7 Hz, 1H), 6.55 (dd, J=9, 2.7 Hz, 1H), 7.39-7.34 (m, 2H) 7.62-7.7 (m, 2H), 7.84-7:89 (m, 2H), 8.2 (d, J=9.0 Hz, 1H), 8.5 (dd, J=7.9, 1.4 Hz, 1H), 8.6 (dd, J=7.9, 1.3 Hz, 1H); $^{13}$C NMR (101 MHz, CDCl$_3$) δ ppm 13.9, 20.2, 29.4, 50.9, 51.1, 96.3, 97.3, 109.4, 116.6, 123.8, 123.9, 124.0, 125.0, 125.3, 127.3, 128.3, 129.9, 130.1, 130.5, 130.6, 131.0, 146.6, 149.5, 150.7, 157.2; MS (EI$^+$): m/z: 451 [M×+1]$^+$; HRMS (EI$^+$) 450.2406 [M×]$^+$, found 450.2409.

3-Bromo-N,N-diethyl-5-(pyridin-2-ylimino)-5H-benzo[a]phenoxazin-9-amine (1F)

Yield 73%, mp 204-205° C.; IR ν (neat, cm$^{-1}$): 2980, 1640, 1590, 1580, 1490, 1455, 1320, 1250, 1115; UV-vis (CHCl$_3$): λ (nm) (log ε/L mol$^{-1}$cm$^{-1}$): 544 (4.62); $^1$H NMR (400 MHz, CDCl$_3$) δ ppm 1.21 (t, J=7.1 Hz, 6H), 3.40 (q, J=7.1 Hz, 4H), 6.26 (d, J=2.6 Hz, 1H), 6.47 (s, 1H), 6.55 (dd, J=9.0, 2.7 Hz, 1H), 7.04 (t, J=6.3 Hz, 2H), 7.46 (d, J=9.0 Hz, 1H), 7.70-7.74 (m, 2H), 8.44 (d, J=8.6 Hz, 1H), 8.50-8.51 (m, 1H), 8.78 (d, J=2.0 Hz, 1H); $^{13}$C NMR (101 MHz, CDCl$_3$) 5 ppm 12.6, 45.0, 96.3, 99.1, 108.9, 117.2, 118.9, 124.7, 124.8, 125.5, 128.2, 130.4, 133.1, 134.1, 137.7, 140.8, 146.7, 148.9, 149.0, 150.2, 156.7, 163.2; MS (Cr): m/z: 473 [MH]$^+$; HRMS (CI$^+$) 473.0976 [MH]$^+$, found 473.0981. Anal. Calcd. For $C_{25}H_{21}BrN_4O \times 3H_2O$: C, 56.93; H, 5.16; N, 10.62. Found: C, 57.41; H, 4.35; N, 10.01.

3-Bromo-N,N-diethyl-5-(pyridin-4-ylimino)-5H-benzo[a]phenoxazin-9-amine 1G)

Yield 28%, mp 269-271° C.; IR ν (neat, cm$^{-1}$): 2980, 1635, 1590, 1575, 1490, 1410, 1355, 1250, 1115; UV-vis (CHCl$_3$): λ (nm) (log ε/L mol$^{-1}$cm$^{-1}$): 720 (4.44), 547 (4.43); $^1$H NMR (400 MHz, CDCl$_3$) δ ppm 1.22 (t, J=7.1 Hz, 6H), 3.41 (q, J=7.1 Hz, 4H), 6.08 (s, 1H), 6.27 (d, J=2.6 Hz, 1H), 6.56 (dd, J=9.0, 2.7 Hz, 1H), 6.84-6.86 (m, 2H), 7.47 (d, J=9.0 Hz, 1H), 7.73 (dd, J=8.6, 2.1 Hz, 1H), 8.44 (d, J=8.6 Hz, 1H), 8.53-8.55 (m, 2H), 8.63 (d, J=2.0 Hz, 1H); $^{13}$C NMR (101 MHz, CDCl$_3$) δ ppm 12.6, 45.0, 96.2, 97.5, 109.1, 116.0, 124.81, 124.85, 125.6, 128.0, 130.3, 130.6, 133.3, 133.5, 140.4, 146.6, 149.1, 150.2, 150.3, 155.7, 159.2; MS (CI$^+$): m/z: 473 [MH]$^+$; HRMS (CI$^+$) 473.0976 [MH]$^+$, found 473.1017. Anal. Calcd. For $C_{25}H_{21}BrN_4O.4H_2O$: C, 73.86; H, 5.77; N, 11.88. Found: C, 73.16; H, 5.29; N, 11.67.

N,N-Diethyl-5-(quinolin-2-ylimino)-5H-benzo[a]phenoxazin-9-amine (1H)

Yield 71%, mp 234-236° C.; IR ν (neat, cm$^{-1}$): 2980, 1635, 1585, 1540, 1510, 1340, 1265, 1220, 1110; UV-vis (CHCl$_3$): λ (nm) (log ε/L mol$^{-1}$cm$^{-1}$): 691 (4.30), 539 (4.57); $^1$H NMR (400 MHz, CDCl$_3$) δ ppm 1.19 (t, J=7.1 Hz, 6H), 3.39 (q, J=7.1 Hz, 4H), 6.26 (d, J=2.7 Hz, 1H), 6.47 (s, 1H), 6.57 (dd, J=9.0, 2.7 Hz, 1H), 7.20 (d, J=8.5 Hz, 1H), 7.44-7.48 (m, 1H), 7.52 (d, J=9.0 Hz, 1H), 7.63-7.70 (m, 3H), 7.79-7.83 (m, 1H), 8.03 (d, J=8.4 Hz, 1H), 8.14-8.16 (m, 1H), 8.62-8.72 (m, 2H); $^{13}$C NMR (101 MHz, CDCl$_3$) δ ppm 12.6, 44.9, 96.3, 99.3, 108.9, 117.6, 123.7, 124.8, 124.9, 125.6, 125.7, 127.4, 128.5, 129.5, 129.8, 130.3, 130.4, 130.5, 131.7, 132.5, 137.8, 146.7, 148.0, 149.2, 150.0, 156.4, 158.2; MS (EI$^+$): m/z: 444 [M×]$^+$; HRMS (EI$^+$) 444.1950 [M×]$^+$, found 444.1931. Anal. Calcd. For $C_{29}H_{24}N_4O \times 1.5H_2O$: C, 73.86; H, 5.77; N, 11.88. Found: C, 73.16; H, 5.29; N, 11.67.

5-(6-Chlorobenzo[d]thiazol-2-ylimino)-N,N-diethyl-5H-benzo[a]phenoxazin-9-amine (1I)

Yield 45%, mp 229-231° C.; IR ν (neat, cm$^{-1}$): 2975, 1640, 1585, 1545, 1510, 1460, 1420, 1320, 1220, 1110; UV-vis (CHCl$_3$): λ (nm) (log ε/L mol$^{-1}$cm$^{-1}$): 583 (4.62); $^1$H NMR (400 MHz, CDCl$_3$) δppm 1.24 (t, J=7.1 Hz, 6H), 3.44 (q, J=7.1 Hz, 4H), 6.40 (d, J=2.6 Hz, 1H), 6.64 (dd, J=9.1, 2.6 Hz, 1H), 7.37 (d, J=8.6, 2.1 Hz, 1H), 7.57 (d, J=9.1 Hz, 1H), 7.59 (s, 1H), 7.62-7.71 (m, 2H), 7.75 (d, J=2.1 Hz, 1H), 7.80 (d, J=8.6 Hz, 1H), 8.64-8.66 (m, 2H); $^{13}$C NMR (101 MHz, CDCl$_3$) δ ppm 12.6, 45.1, 96.2, 100.4, 109.9, 120.7, 122.5, 123.7, 125.7, 125.9, 126.4, 129.0, 129.8, 130.6, 131.0, 131.6, 132.1, 136.2, 140.4, 146.9, 150.5, 150.7, 151.4, 157.9, 160.3; MS (CI$^+$): m/z: 485 [MH]$^+$; HRMS (CI$^+$) 485.1203 [MH]$^+$, found 485.1268. Anal. Calcd. For $C_{27}H_{21}ClN_4OS \times 0.5H_2O$: C, 65.64; H, 4.49; N, 11.34. Found: C, 65.39; H, 4.42; N, 10.97.

N,N-Diethyl-5-(5-methylisoxazol-3-ylimino)-5H-benzo[a]phenoxazin-9-amine (1J)

Yield 34%, mp 195-196° C.; IR ν (neat, cm$^{-1}$): 2975, 1635, 1590, 1560, 1490, 1275, 1110; UV-vis (CHCl$_3$): λ (nm) (log ε/L mol$^{-1}$cm$^{-1}$): 539 (4.65); $^1$H NMR (400 MHz, CDCl$_3$) δ ppm 1.23 (t, J=7.1 Hz, 6H), 2.45 (s, 3H), 3.42 (q, J=7.1 Hz, 4H), 5.92 (s, 1H), 6.33 (d, J=2.7 Hz, 1H), 6.58 (dd, J=9.0, 2.7 Hz, 1H), 6.77 (s, 1H), 7.51 (d, J=9.0 Hz, 1H), 7.60-7.68 (m, 2H), 8.59-8.63 (m, 2H); $^{13}$C NMR (101 MHz, CDCl$_3$) δ ppm 12.6, 12.7, 44.9, 96.3, 99.1, 99.6, 109.0, 123.7, 125.0, 125.5, 129.8, 130.3, 130.5, 131.5, 132.3, 141.3, 146.7, 149.2, 150.1, 160.3, 168.8, 169.6; MS (EI$^+$): m/z: 398 [M×]$^+$; HRMS (EI$^+$) 398.1742 [M×]$^+$, found 398.1721. Anal. Calcd. For $C_{24}H_{22}N_4O_2 \times 2H_2O$: C, 66.34; H, 6.03; N, 12.89. Found: C, 66.54; H, 5.43; N, 12.67.

5-(3,5-Dichloropyridin-2-ylimino)-N,N-diethyl-5H-benzo[a]phenoxazin-9-amine (1K)

Yield 10%, mp 192-193° C.; IR ν (neat, cm$^{-1}$): 2980, 1640, 1590, 1555, 1420, 1275, 1210, 1115; UV-vis (CHCl$_3$): λ (nm) (log ε/L mol$^{-1}$cm$^{-1}$): 547 (4.67); $^1$H NMR (400 MHz, CDCl$_3$) δ ppm 1.22 (t, J=7.1 Hz, 6H), 3.43 (q, J=7.1 Hz, 4H), 6.34 (d, J=2.6 Hz, 1H), 6.42 (s, 1H), 6.61 (dd, J=9.0, 2.5 Hz, 1H), 7.54 (d, J=9.0 Hz, 1H), 7.63-7.71 (m, 2H), 7.78 (d, J=2.3 Hz, 1H), 8.34 (d, J=2.3 Hz, 1H), 8.63-8.69 (m, 2H); $^{13}$C NMR (101 MHz, CDCl$_3$) δ ppm 12.6, 45.0, 96.3, 98.8, 109.3, 123.7, 124.6, 125.2, 125.6, 125.8, 129.9, 130.4, 130.7, 131.6, 132.0, 137.3, 141.1, 145.4, 146.7, 149.4, 150.3, 158.5, 158.8; MS (EI$^+$): m/z: 462 [M×]$^+$; HRMS (EI$^+$) 462.1014 [M×]$^+$, found 462.0958. Anal. Calcd. For $C_{25}H_{20}Cl_2N_4O \times 0.5H_2O$: C, 63.57; H, 4.48; N, 11.86. Found: C, 63.48; H, 4.30; N, 11.72.

N,N-Diethyl-5-(pyrimidin-2-ylimino)-5H-benzo[a]phenoxazin-9-amine (1 L)

Yield 24%, mp 208-210° C.; IR ν (neat, cm$^{-1}$): 2975, 1640, 1590, 1550, 1395, 1275, 1110; UV-vis (CHCl$_3$): λ (nm) (log ε/L mol$^{-1}$cm$^{-1}$): 543 (4.62); NMR (400 MHz, CDCl$_3$) δ ppm 1.23 (t, J=7.1 Hz, 6H), 3.43 (q, J=6.9 Hz, 1H), 6.34 (d, J=2.1 Hz, 1H), 6.58 (s, 1H), 6.63 (dd, J=9.0, 2.3 Hz, 1H), 7.02 (t, J=4.8 Hz, 1H), 7.54 (d, J=9.0 Hz, 1H), 7.61-7.70 (m, 2H), 8.63 (d, J=7.7 Hz, 1H), 8.67 (d, J=8.1 Hz, 1H), 8.74 (d, J=4.8 Hz, 2H); $^{13}$C NMR (101 MHz, CDCl$_3$) δ ppm 12.6, 45.01, 96.2, 99.3, 109.6, 115.6, 123.6, 125.4, 125.7, 129.8, 130.5, 130.8, 131.6, 131.9, 140.9, 146.7, 149.4, 150.4, 158.6, 159.0, 168.1; MS (EI$^+$): m/z: 395 [M×]$^+$; HRMS (CI$^+$) 396.1824 [MH]$^+$, found 396.1850. Anal. Calcd. For $C_{24}H_{21}N_5O \times 1.5H_2O$: C, 68.23; H, 5.73; N, 16.58. Found: C, 68.60; H, 5.29; N, 16.34.

N,N-Diethyl-5-(6-methoxybenzo[d]thiazol-2-ylimino)-5H-benzo[a]phenoxazin-9-amine (1M)

Yield 52%, mp 197-198° C.; IR ν (neat, cm$^{-1}$): 2975, 1635, 1585, 1430, 1320, 1270, 1110; UV-vis (CHCl3): λ (nm) (log ε/L mol$^{-1}$cm$^{-1}$): 582 (4.69); $^1$H NMR (400 MHz, CDCl$_3$) δ ppm 1.23 (t, J=7.1 Hz, 6H), 3.43 (q, J=7.1 Hz, 4H), 3.89 (s, 3H), 6.39 (d, J=2.7 Hz, 1H), 6.62 (dd, J=9.1, 2.7 Hz, 1H), 7.03 (dd, J=8.9, 2.6 Hz, 1H), 7.29 (d, J=2.5 Hz, 1H), 7.55 (d, J=9.0 Hz, 1H), 7.62-7.70 (m, 3H), 7.81 (d, J=8.9 Hz, 1H), 8.64-8.69 (m, 2H); $^{13}$C NMR (101 MHz, CDCl$_3$) δ ppm 12.6, 45.0, 55.8, 96.2, 100.7, 104.2, 109.7, 114.7, 122.5, 123.7, 125.7, 125.8, 129.7, 130.4, 130.8, 131.6, 132.3, 136.3, 140.8, 146.9, 147.2, 150.2, 150.5, 156.5, 159.4, 160.3; MS (CI$^+$): m/z: 481 [MH]$^+$; HRMS (CI$^+$) 481.1698 [MH]$^+$, found 481.1691. Anal. Calcd. For $C_{28}H_{24}N_4O_2S \times 0.5H_2O$: C, 68.69; H, 5.15; N, 11.44. Found: C, 68.41; H, 5.01; N, 11.23.

N,N-Diethyl-5-(pyridin-3-ylimino)-5H-benzo[a]phenoxazin-9-amine (1N)

Yield 43%, mp 198-199° C.; IR ν (neat, cm$^{-1}$): 2971, 1636, 1589, 1564, 1488, 1469, 1408, 1352, 1271, 1218, 1109, 1014; UV-vis (CHCl$_3$): λ (nm) (log ε/L mol$^{-1}$cm$^{-1}$): 533 (4.46), 240 (4.36); $^1$HNMR (400 MHz, CDCl$_3$) δ ppm 1.21 (t, J=7.1 Hz, 6H), 3.42 (q, J=7.1 Hz, 4H), 6.24 (s, 1H), 6.29 (d, J=2.7 Hz, 1H), 6.57 (dd, J=9.0, 2.7 Hz, 1H), 7.29-7.31 (m, 2H), 7.50 (d, J=9.0 Hz, 1H), 7.63-7.69 (m, 2H), 8.28 (d, J=1.47 HZ, 1H), 8.37 (dd, J=4.33, 1.80 HZ), 8.57 (d, J=7.62 Hz, 1H), 8.64 (dd, J=7.9, 1.3 Hz, 1H); $^{13}$C NMR (101 MHz, CDCl$_3$) δ ppm 12.58, 44.92, 96.3, 97.7, 108.8, 123.6, 123.8, 124.8, 125.07, 128.1, 129.9, 130.2, 130.4, 131.5, 132.4, 141.8, 142.4, 144.5, 146.6, 149.1, 150.02; MS (EI$^+$): m/z: 395.1 [M+1]$^+$; HRMS (EI$^+$) 394.1793 [M×]$^+$, found 394.1792.

N-(9-Morphlino-5H-benzo[a]phenoxazin-5-ylidene)pyridin-2-amine (1O)

Yield 39%, mp 235-236° C.; IR ν (neat, cm$^{-1}$): 3066 2962, 2855, 1636, 1592, 1585, 1551, 1488, 1462 1423, 1332, 1307, 1237, 1123, 772; UV-vis (CHCl$_3$): λ (nm) (log ε/L mol$^{-1}$cm$^{-1}$): 525 (4.38), 225 (4.33); $^1$HNMR (400 MHz, CDCl$_3$) δ ppm 3.38 (t, J=7.2 Hz, 4H), 3.87 (t, J=7.1 Hz, 4H), 6.6 (s, 1H), 6.89 (dd, J=8.9, 2.7 Hz, 1H), 7.12 (t, J=7.8 Hz, 2H), 7.6 (d, J=9.0 Hz, 1H), 7.72-7.74 (t, J=7.3 Hz, 2H), 7.81 (t, J=7.3 Hz, 2H), 8.35 (dd, J=7.9, 1.4 Hz, 1H), 8.5 (d, J=6.7 Hz, 1H), 8.69 (t, J=7.9, Hz, 1H); $^{13}$C NMR (101 MHz, CDCl$_3$) δ ppm 47.7, 66.4, 99.5, 99.8, 106.4, 111.7, 117.6, 119.2, 124.0, 125.8, 127.3, 130.4, 130.5, 130.6, 131.2, 131.6, 138.0, 146.1, 148.5, 148.9, 153.1, 157.5; MS (EI$^+$): m/z: 409.1 [M×+1]$^+$; HRMS (EI$^+$) 408.1586 [M×]$^+$, found 408.1568.

N,N-Diethyl-5-(2-methylquinoline-4-ylimino)-5H-benzo[a]phenoxazin-9-amine (1P)

Yield 38%, mp 229-230° C.; IR ν (neat, cm$^{-1}$): 3059, 2973, 2930, 1637, 1590, 1552, 1489, 1463, 1407, 1352, 1271, 1252, 1113, 770; UV-vis (CHCl$_3$): λ (nm) (log ε/L mol$^{-1}$cm$^{-1}$): 683 (4.10), 537 (4.24); $^1$HNMR (400 MHz, CDCl$_3$) δ ppm 1.18 (t, J=7.1 Hz, 6H), 3.43 (q, J=7.1 Hz, 4H), 2.88 (s, 3H), 6.03 (s, 1H), 6.28 (d, J=2.6 Hz, 1H), 6.58-6.69 (dd, J=8.9, 2.7 Hz, 1H), 6.78 (s, 1H), 7.41-7.74 (m, 6H), 8.2 (d, J=9.0 Hz, 1H), 8.63-8.70 (m, 2H); $^{13}$C NMR (101 MHz, CDCl$_3$) δ ppm 12.5, 25.4, 44.9, 96.3, 98.2, 108.8, 110.0, 121.1, 122.2, 123.8, 123.9, 124.7, 124.8, 125.3, 126.2, 126.5, 126.9, 127.9, 128.4, 129.6, 130.0, 130.3, 130.5, 131.2, 131.6, 132.1, 141.5, 146.6, 149.1, 150.0, 157.3, 159.3, 159.7; MS (EI$^+$): m/z: 459.1 [M×+1]+; HRMS (EI$^+$) 458.2106 [M×]$^+$, found 458.2125.

Ethyl 2-[9-(Diethylamino)-5H-benzo[a]phenoxazin-5-ylideneamino]-3-(4-hydroxyphenyl)propanoate (1Q)

Yield 37%, mp 175-1'76° C.; IR ν (neat, cm$^{-1}$): 3312, 3066, 2978, 2934, 1734, 1637, 1586, 1515, 1444, 1409, 1376, 1354, 1272, 1252, 1170, 1014; UV-vis (CHCl$_3$): λ (nm) (log ε/L mol$^{-1}$cm$^{-1}$): 539 (4.41), 387 (4.04); $^1$H NMR (400 MHz, CDCl₃) δ ppm 1.22 (t, J=7.1 Hz, 6H), 1.37 (t, J=7.13 Hz, 3H), 3.43 (q, J=7.1 Hz, 4H), 4.82 (q, J=7.1 Hz, 2H), 6.17 (s, 1H), 6.30 (d, J=2.7 Hz, 1H), 6.55-658 (dd, J=8.95, 2.58 Hz, 1H), 6.76 (d, J=8.46 Hz, 2H), 6.99 (d, J=8.43 Hz, 2H), 7.49-7.50 (m, 2H), 7.67-7.81 (m, 2H), 8.63-8.69 (dd, J=8.95, 2.58 HZ, 1H), 9.87 (s, 1H), $^{13}$C NMR (101 MHz, CDCl₃) δ ppm 12.5, 14.2, 36.9, 44.5, 53.8, 61.9, 96.2, 98.6, 109.5, 122.3, 123.9, 123.8, 125.02, 125.7, 128.8, 129.9, 130.2, 130.5, 131.3, 132.5, 146.6, 148.3, 150.4, 155.3, 156.1, 170.4; MS (EI⁺): m/z: 510 [M.]⁺; HRMS (EI⁺) 510.2393 [M×]⁺, found 510.2413.

N-Ethyl-N-(2-methansulfonamidylethyl)-11-methyl-5-(pyridine-4-ylimino)-5H-benzo[a]phenoxazin-9-amine (1R)

Yield 38%, mp 235-236° C.; IR ν (neat, cm⁻¹): 3633, 3023, 2972, 1639, 1605, 1581, 1556, 1491, 1412, 1370, 1313, 1219, 1136; $^1$H NMR (400 MHz, CDCl₃) δ ppm 1.21 (t, J=7.01 Hz, 3H), 2.6 (s, 3H), 2.97 (s, 3H), 3.35 (q, J=6.62 Hz, 2H), 3.47 (q, J=7.0 Hz, 2H), 3.58 (t, J=6.62 Hz, 2H), 6.13 (s, 1H), 6.24 (d, J=2.41 Hz, 1H), 6.51 (s, 1H), 6.86 (d, J=5.58 Hz, 1H), 7.65-7.69 (m, 2H), 8.51-8.54 (m, 3H), 8.68 (ddJ=7.46, Hz, 1H); MS (EI⁺): m/z: 502.3 [M×+1]⁺

1R.HCl mp>300; IR ν (neat, cm⁻¹): 3062, 2979, 2864, 1639, 1580, 1512, 1444, 1364, 1320, 1236, 1194, 1079; NMR (400 MHz, CDCl₃) δ ppm 1.21 (t, J=7.01 Hz, 3H), 2.6 (s, 3H), 2.87 (s, 3H), 3.14 (q, J=6.62 Hz, 2H), 3.49 (t, J=6.62 Hz, 2H), 5.99 (s, 1H), 6.42 (d, J=2.41 Hz, 1H), 6.67 (s, 1H), 6.91 (d, J=5.58 Hz, 1H), 7.19-7.2 (t, J=6.24 Hz, 1H), 7.69-7.81 (m, 2H), 8.45 (ddJ=7.96, 1.11 Hz, 1H), 8.51 (dd J=4.56, 157, Hz, 2H), 8.59 (dd J=7.96, 0.99, Hz, 1H); MS (EI⁺): m/z: 503.2 [M×+1]⁺.

N-Ethyl-N-(2-methansulfonamidylethyl)-11-methyl-5-(pyridine-2-ylimino)-5H-benzo[a]phenoxazin-9-amine (1S)

Yield 41%, mp 221-222° C.; IR ν (neat, cm⁻¹): 3632, 3065, 2979, 1634, 1593, 1580, 1549, 1488, 1462, 1370, 1320, 1272, 1147, 772; $^1$H NMR (400 MHz, CDCl₃) δ ppm 1.14 (1, J=7.1 Hz, 3H), 2.53 (s, 3H), 2.96 (s, 3H), 3.32 (q, J=6.7 Hz, 2H), 3.38 (q, J=7.12 Hz, 2H), 3.51 (t, J=6.76 Hz, 2H), 6.31 (s, 1H), 6.5 (d, J=8.27 Hz, 1H), 6.64 (t, J=7.27 Hz, 1H), 6.96 (d, J=8.01 Hz, 1H), 7.01-7.06 (t, J=7.1 Hz, 1H), 7.44 (t, J=7.01 Hz, 1H), 7.64-7.7 (m, 2H), 8.06 (d, J=4.15 Hz, 1H), 8.51-8.6 (m, 2H); MS (EI⁺): m/z: 502.3 [M×+1]⁺

N-Ethyl-N-(2-methansulfonamidy lethyl)-11-methyl-5-(pyridine-3-ylimino)-5H-benzo[a]phenoxazin-9-amine (1T)

Yield 45%, mp 227-228° C.; IR ν (neat, cm⁻¹): 3620, 3065, 2975, 1634, 1591, 1554, 1488, 1411, 1319, 1272, 1218, 1147, 772; $^1$H NMR (400 MHz, CDCl₃) δ ppm 1.2 (t, J=7.02 Hz, 3H), 2.61 (s, 3H), 2.97 (s, 3H), 3.35 (q, J=6.62 Hz, 2H), 3.46 (q, J=7.0 Hz, 2H), 3.57 (t, J=6.56 Hz, 2H), 6.2 (m, 2H), 6.49 (d, J=1.98 Hz, 1H), 7.29-7.31 (m, 2H), 7.65-7.67 (m, 2H), 8.25 (d, J=1.59 Hz, 1H), 8.37 (dd, J=4.36, 1.66 Hz, 1H), 8.61 (dd, J=7.9, 1.3 Hz, 1H), 8.684 (dd J=7.46, 1.3 Hz, 1H); MS (EI⁺): m/z: 502.3 [M×+1]⁺

N,N-Diethyl-11-methyl-5-(pyridin-2-ylamino)-5H-benzo[a]phenoxazin-9-amine (1a)

Yield 13.8%, 1a.HCl mp 167.2-168.4° C.; IR ν (neat, cm⁻¹): 2978, 1638, 1594, 1577, 1530, 1446, 1245, 1196, 1124, 870, 780; UV-vis (MeOH): λ (nm) (log ε/L mol⁻¹cm⁻¹): 668 (4.85); $^1$H NMR (400 MHz, MeOH) d ppm 8.86 (d, J=8.0 Hz, 1H), 8.62 (s, 1H), 8.48 (d, J=8.2 Hz, 1H), 8.41 (d, J=4.6 Hz, 1H), 7.94 (t, J=8.0 Hz, 1H), 7.84 (t, J=7.5, 1H), 7.78 (t, J=7.5, 1H), 7.51 (d, J=8.2 Hz, 1H), 7.37 (s, 1H), 7.30-7.19 (m, 1H), 6.89 (d, J=2.4 Hz, 1H), 3.80 (q, J=7.1 Hz, 4H), 2.73 (s, 3H), 1.39 (t, J=7.1 Hz, 6H); $^{13}$C NMR (101 MHz, MeOD) d ppm 159.5, 153.0, 151.5, 147.4, 146.7, 145.6, 145.2, 142.4, 141.4, 132.6, 131.9, 131.2, 130.0, 126.8, 124.6, 124.3, 122.4, 119.3, 117.5, 107.5, 97.3, 36.7, 17.5, 13.6; MS (ESI⁻⁴): m/z: 409.1 [M⁺]; Anal. Calcd. For C₂₆H₂₅ClN₄O×4.5H₂O: C, 59.37; H, 6.51; N, 10.65. Found: C, 59.24; H, 5.66; N, 10.55.

N,N-Diethyl-11methyl-5-(pyridin-3-ylamino)-5H-benzo[a]phenoxazin-9-amine (1b)

Yield 18.2%, 1b.HCl mp 161.6-163.1° C.; IR ν (neat, cm⁻¹): 2978, 1639, 1585, 1546, 1449, 1381, 1321, 1249, 1198, 1125, 1089, 988; UV-vis (MeOH): λ (nm) (log e/L mol⁻¹cm⁻¹): 656 (4.64); $^1$H NMR (400 MHz, MeOD) d ppm 9.13 (d, J=8.4 Hz, 1H), 9.02 (d, J=2.4 Hz, 1H), 8.68 (d, J=5.0 Hz, 1H), 8.66 (d, J=2.4 Hz, 1H), 8.53 (d, J=8.4 Hz, 1H), 8.12 (dd, J=8.4, 5.0 Hz, 1H), 8.02 (t, J=7.6 Hz, 1H), 7.91 (m, 1H), 7.57 (m, 1H), 7.54 (s, 1H), 7.05 (d, J=2.4 Hz, 1H), 3.87 (q, J=7.2 Hz, 4H), 2.86 (s, 3H), 1.40 (t, J=7.2 Hz, 6H); $^{13}$C NMR (101 MHz, MeOD) d ppm 158.6, 151.7, 151.6, 149.9, 146.3, 141.9, 169.6, 139.4, 138.8, 137.4, 133.0, 132.4, 131.2, 130.0, 129.4, 125.4, 125.0, 124.3, 120.9, 99.0, 96.5, 39.8, 17.4, 13.6; MS (ESI⁺): m/z: 409.1 [M⁺]; Anal. Calcd. For C₂₆H₂₅ClN₄O×4.5H₂O: C, 59.37; H, 6.51; N, 10.65. Found: C, 59.63; H, 5.36; N, 10.56.

N,N-Diethyl-11-methyl-5-(pyridin-4-ylamino)-5H-benzo[a]phenoxazin-9-amine (1c)

Yield 26.6%, 1c.HCl mp>300° C.; IR ν (neat, cm⁻¹): 2977, 1639, 1579, 1513, 1443, 1324, 1249, 1199, 1072, 946, 823, 780; UV-vis (MeOH): λ (nm) (log e/L mol⁻¹cm⁻¹): 594 (4.22); $^1$HNMR (400 MHz, MeOD) d ppm 9.16 (d, J=8.4 Hz, 1H), 8.43 (d, J=7.4 Hz, 2H), 8.31 (d, J=8.4 Hz, 1H), 8.06-7.96 (m, 2H), 7.86-7.90 (m, 1H), 7.79 (s, 1H), 7.56 (d, J=7.4 Hz, 2H), 7.25 (d, J=2.5 Hz, 1H), 4.0 (q, J=7.0 Hz, 4H), 2.89 (s, 3H), 1.46 (t, J=7.0 Hz, 6H); $^{13}$C NMR (101 MHz, MeOD) d ppm 160.2, 158.7, 152.0, 147.3, 146.5, 144.6, 144.4, 142.5, 132.9, 131.9, 131.5, 130.0, 127.9, 124.8, 124.7, 123.4, 112.9, 110.5, 97.6, 39.5, 17.5, 14.1; MS (ESI⁺): m/z: 394 [M⁺]; Anal. Calcd. For C₂₆H₂₅ClN₄O×4.5H₂O: C, 59.37; H, 6.51; N, 10.65. Found: C, 58.51; H, 5.57; N, 10.52.

N,N-Dimethyl-5-(pyridin-4-ylimino)-5H-benzo[a]phenoxazin-9-amine (1d)

Yield 14.1%, mp>300° C.; IR ν (neat, cm⁻¹): 1641, 1599, 1579, 1486, 1401, 1366, 1337, 1263, 1201, 1133, 1114, 986, 809, 769; UV-vis (CHCl₃): λ (nm) (log e/L mol⁻¹cm⁻¹): 532 (4.67); NMR (400 MHz, CDCl₃) d ppm 8.64 (dd, J=7.8, 1.6 Hz, 1H), 8.54 (dd, J=4.8, 1.5 Hz, 2H), 8.52 (d, J=1.6 Hz, 1H), 7.77-7.59 (m, 2H), 7.55 (d, J=9.0 Hz, 1H), 6.86 (dd, J=4.8, 1.5 Hz, 2H), 6.60 (dd, J=9.0, 2.7 Hz, 1H), 6.33 (d, J=2.7 Hz, 1H), 6.15 (s, 1H), 3.07 (s, 6H); $^{13}$C NMR (101 MHz, CDCl₃) d ppm 159.9, 156.9, 152.3, 149.7, 149.2, 146.3, 142.0, 132.2, 131.5, 130.5, 130.3, 130.1, 125.2, 125.1, 124.0, 116.2, 109.3, 97.9, 96.9, 40.3; MS (ESI⁺): m/z: 367.1 [M+H]⁺; Anal. Calcd. For C₂₃H₁₈N₄O×0.5H₂O: C, 73.58; H, 5.10; N, 14.92. Found: C, 73.27; H, 4.85; N, 14.62.

9-Morpholino-5-(pyridin-4-ylimino)-5H-benzo[a]phenoxazine (1e)

Yield 14.5%, mp>300° C.; IR ν (neat, cm⁻¹): 2968, 2835, 1635, 1595, 1578, 1510, 1488, 1239, 1121, 1110, 1043, 1003, 827, 755; UV-vis (CHCl$_3$): λ (nm) (log e/L mol$^{-1}$cm$^{-1}$): 502 (4.49); $^1$H NMR (400 MHz, CDCl$_3$) d ppm 8.69-8.62 (m, 1H), 8.54 (dd, J=4.8, 1.5 Hz, 2H), 8.51 (d, J=2.2 Hz, 1H), 7.77-7.63 (m, 2H), 7.58 (d, J: 8.9, 1H), 6.85 (dd, J=4.8, 1.5 Hz, 2H), 6.78 (dd, J=8.9, 2.6 Hz, 1H), 6.52 (d, J=2.6, 1H), 6.15 (s, 1H), 3.86 (t, J=4.8 Hz, 4H), 3.29 (t, J=4.8 Hz, 4H); $^{13}$C NMR (101 MHz, CDCl$_3$) d ppm 159.1, 156.5, 152.8, 150.2, 148.7, 145.8, 144.0, 132.4, 131.2, 130.5, 130.4, 130.1, 126.6, 125.2, 124.1, 115.9, 111.2, 99.7, 98.4, 66.4, 47.6; MS (ESI$^+$): m/z: 409.2 [M+H]$^+$; Anal. Calcd. For C$_{25}$H$_{20}$N$_4$O$_2$× 0.5H$_2$O: C, 71.93; H, 5.07; N, 13.42. Found: C, 72.15; H, 5.08; N, 12.23.

9-(Piperidin-1-yl)-5-(pyridin-4-ylimino)-5H-benzo[a]phenoxazine (1f)

Yield 1.5%, mp 266.8-268.2° C.; IR ν (neat, cm$^{-1}$): 2931, 2850, 1635, 1595, 1577, 1485, 1239, 1112, 1000, 827, 756; UV-vis (CHCl$_3$): λ (nm) (log e/L mol$^{-1}$cm$^{-1}$): 530 (4.52); $^1$H NMR (400 MHz, CDCl$_3$) d ppm 8.68-8.61 (m, 1H), 8.54 (dd, J=4.6, 1.5 Hz, 2H), 8.51 (d, J=1.8 Hz, 1H), 7.71-7.63 (m, 2H), 7.53 (d, J=9.0 Hz, 1H), 6.86 (dd, J=4.6, 1.5 Hz, 2H), 6.78 (dd, J=9.0, 2.7 Hz, 1H), 6.51 (d, J=2.7 Hz, 1H), 6.14 (s, 1H), 3.35 (t, J=5.0 Hz, 4H), 1.71-1.65 (m, 6H); $^{13}$C NMR (101 MHz, CDCl$_3$) d ppm 159.7, 156.9, 153.0, 149.8, 149.1, 146.1, 142.6, 132.1, 131.3, 130.5, 130.3, 130.1, 125.7, 125.1, 124.0, 116.3, 111.6, 99.3, 97.9, 48.8, 25.2, 24.2; MS (ESI$^+$): m/z: 407.1 [M+H]$^+$; Anal. Calcd. For C$_{26}$H$_{22}$N$_4$O: C, 76.83; H, 5.46; N, 13.78. Found: C, 76.15; H, 5.47; N, 13.77.

[Activity Against Drug-Resistant *Plasmodium* Falciparam and Selective Toxicity (In vitro)]

1. Culture of Chloroquine Resistant-*Plasmodium falciparum*

In the present experiment, protozoa of *plasmodium* falsiparum K1 strain was used. RPMI-1640 medium sterilized with a filter to which human serum was added to be 5%, was used in the experiment. Malarial parasites were cultured under 3% O$_2$ concentration, 4% CO$_2$ concentration, 93% N$_2$ concentration, and at a temperature of 37° C.

2. Chloroquine Resistant-*Plasmodium falciparum* Growth Inhibition Screening Test The compounds of the present invention to be used in the present test and the positive control drug (chloroquine) were dissolved in DMSO to make a test solution of a predetermined concentration. Cultured malaria parasite infected-erythrocytes were collected by centrifugation, and diluted with non-infected erythrocyte so that the early infection rate was 0.15%. Hematocrit level at that time was 2.5%.

200 μL of malaria infected solution was added to wells of a 96-well culture plate, and adjusted by adding a test solution containing drug of a predetermined concentration or a drug-free DMSO. Test solutions were taken by duplicates.

After culturing for 48 hours at 37° C., 0.5 μCi radioactive tritium (3H)-labeled hypoxanthine was added to each well. After further culturing for 24 hours under the same conditions, it was collected on a glass fiber filter and washed with distilled water. Radiation intensity was measured with a beta plate liquid scintillation counter (Wallac), and malarial parasite infection rates of the test solution added group and the control group were calculated.

Growth inhibition rate is calculated with the following formula based on the malarial parasite infection rate obtained in the above, to obtain a 50% growth inhibition concentration (EC$_{50}$).

Growth inhibition rate (%)={1−(b−a)/(c−a)}×100 a: early infection rate
b: infection rate when test solution was added
c: infection rate of the control 3. Growth Inhibition Test of Rat L6 Cells Rat derived-L6 cells (rat skeletal myoblast cell) were used. A medium, RPMI1640 medium was supplemented so that L-glutamin (200 mM) is 1%, and fetal bovine serum 10%, and the medium was cultured under CO$_2$ concentration 5%, at 37° C.

The compounds of the present invention and the control drugs to be used in the test were dissolved in DMSO, to make a test solution of a predetermined concentration.

Pre-culture was conducted and medium containing cells which have entered the logarithmic growth phase was taken to wells of a 96-well culture plate. Then, a test solution containing drug of a predetermined concentration or a drug-free DMSO was added. Test solutions were taken by duplicates.

Culture plate was cultured for 72 hours in an incubator, to test the growth inhibition activity. Test was conducted as follows. 10 μL of Alamar Blue aqueous solution was added to each well, and the resultant was further cultured for 2 hours. Next, the culture plate was placed on a fluorescent microplate reader (Spectramax Gemeni XS; US Molecular Device), radiated at an excited wavelength of 536 nm. Fluorescent intensity was measured at 588 nm, and residual rate of L6 cells of the test solution added group, and that of the control was calculated.

Based on the cell residual rate obtained in the above, growth inhibition rate to L6 cells was calculated, to obtain a 50% growth inhibition concentration (EC$_{50}$).

Growth inhibition rate (%)={(C−A)/(B−A)}×100

A: Primary cell count
B: cell count of control, 3 days after
C: cell count of wells added with a sample, 3 days after 4. Determination of Drug Efficacy Against Chloroquine Resistant-Plasmodium Antimalarial activity of a sample was estimated from EC$_{50}$ values of the sample against chloroquine resistant-*Plasmodium falciparum* and rat L6 cells. Chemotherapy index used as an index of selective toxicity against chloroquine resistant-plasmodium faciparum was calculated with the following formula, to determine drug efficacy. It means that the larger the value of the selection toxity, the less the risk of the side effect is.

Chemotherapy index=(EC$_{50}$ value of a sample against rat L6 cells)/(EC$_{50}$ value of a sample against chloroquine resistant-*Plasmodium falsiparum*)

EC$_{50}$ values of a sample of the compounds of the present invention and the positive control drug against chloroquine resistant-*Plasmodium falciparum* and rat L6 cells, as well as selective toxicity index are shown in Tables 1 and 2.

As shown in Table 1 below, the benzo[a]phenoxazine compounds were confirmed to show strong killing capabilities to drug-resistant *plasmodium* falciparam (*Plasmodium falciparum* K1) and to have higher selective toxicity to the parasites than to normal cells (L-6) of rat.

TABLE 1

| | 50% Growth inhibition concentration (μg/ml) | | |
|---|---|---|---|
| Compound | P. falciparum K1 | Cytoxicity L6 | Selective toxicity |
| 1A | 0.006 | 6.22 | 1037 |
| 1B | 0.003 | 21.96 | 7320 |
| 1F | 0.018 | >90 | >5000 |

TABLE 1-continued

| Compound | 50% Growth inhibition concentration (μg/ml) | | Selective toxicity |
|---|---|---|---|
| | *P. falciparum* K1 | Cytoxicity L6 | |
| 1G | 0.005 | >90 | >18000 |
| 1H | 0.012 | 30.15 | 2513 |
| 1I | 0.428 | >90 | 210 |
| 1J | 0.005 | 36.8 | 7360 |
| 1K | 0.029 | 83.1 | 2866 |
| 1L | 0.002 | 5.4 | 2700 |
| 1M | 0.054 | 80.6 | 1492 |
| Chloroquine | 0.047 | No data | No data |

TABLE 2

| Compound | *P. falciparum* K1 | Cytoxicity L6 | Selective toxicity |
|---|---|---|---|
| 1N | 0.009 | 46.11 | 5123 |
| 1O | 0.015 | 20.8 | 1386 |
| 1P | 0.036 | 6.6 | 183 |
| 1Q | 0.045 | 33.8 | 751 |
| 1R | 0.009 | 7.97 | 885 |
| 1S | 0.007 | 0.307 | 43 |
| 1T | 0.008 | 23.91 | 2988 |
| 1a | 0.014 | 6.83 | 487 |
| 1b | 0.011 | 39.79 | 3617 |
| 1c | 0.008 | 38.52 | 481 |

[Cure Test by Oral Administration to Mice Infected with Malaria (In Vivo)]

In this experiment, rodent malaria parasites (the *Plasmodium berghei* NK65 strain) were used.

The infected blood to be used was subcultured in ICR female SPF mice infected by intraperitoneal or tail vein administration at 4 to 6 weeks old (20 to 26 g). By collecting blood from the tail vein of the mice infected with malaria, the infection rates were calculated, and after confirming that they showed appropriate levels of infection (an infection rate of 10 to 20%), malaria-infected blood was collected from the heart of the mice with a heparin-containing syringe. Thereafter, based on the number of red cells (cells/ml) and the rate of infection by the protozoans, the blood was diluted with phys'iological saline such that a density of $5.0 \times 10^{-6}$ malaria parasites/1 ml dose was attained. This was used for infection of uninfected mice (ICR female mice, 5 weeks old) in an amount of 0.2 ml/20 g body weight, through the tail vein (Day-0). The compound used in the test was dissolved in 10% DMSO solution (a mixture of 1 ml of DMSO and 9 ml of 5% glucose solution).

Each group contained 4 mice, and the compound was orally administered to the mice 24 hours after their infection with malaria (Day-1), in an amount calculated such that 100 mg of the compound was administered per 1 kg of the body weight of a mouse. On the other hand, in terms of cases in which the amount was calculated such that 30 mg of the compound was administered per 1 kg of the body weight of a mouse, the oral administration was carried out a total of three times, that is, 24 hours (Day-1), 48 hours (Day-2) and 72 hours (Day-3) after the infection of malaria.

Blood was collected from the tails of each mouse 96 hours (Day-4) and 144 hours (Day-6) after the infection with malaria, and thin blood films were prepared. Under the microscope, the numbers of infection of malaria parasites in the group to which the compound was administered and the control group (to which the compound was not administered) were measured, and the rates of infection with malaria parasites (Parasitemia) were calculated.

From the rate of infection with malaria parasites calculated as above, the cure rate (Suppression) in the case of administration of the drug was calculated according to the following equation.

Cure rate: Suppression $(\%) = (B-A)/B \times 100$

A: Rate of infection with the protozoans in a mouse to which the present test compound was administered
B: Rate of infection with the parasites in a control mouse (to which the compound was not administered)

Days of survival: $MSD$ (day)$=C-D$

C: the average number of days from the date of infection with malaria to the date of death in the mice to which the present test compound was administered
D: The average number of days from the date of infection with malaria to the date of death in the 4 individuals of control mice (to which the compound was not administered)

Further, by observation of changes in the body weight, hair glossiness and the like of each mouse, side effects such as acute toxicity due to administration of the compound were evaluated. The results obtained by the above experiments are shown in Table 3 and Table 4 below.

TABLE 3

| Compound | Dose (mg/kg) | Number of doses | Cure rate (%) Day-4 | Cure rate (%) Day-6 | Days of survival (days) |
|---|---|---|---|---|---|
| 1A | 100 | 1 | 100 | 97 | 2.3 |
| 1B | 100 | 1 | 100 | 99 | 14.6 |
| 1B | 100 | 3 | 100 | 100 | Not less than 30 days (completely cured) |
| 1A | 30 | 3 | 85 | 99 | 15.0 |
| 1B | 30 | 3 | 98 | 99 | Not less than 60 days (completely cured) |
| 1H | 100 | 1 | 81 | 71 | 4.3 |
| 1N | 100 | 1 | 41 | 0 | 0 |
| 1O | 100 | 1 | 81 | 60 | 0.6 |
| 1R | 100 | 1 | 100 | 95.7 | 15.7 |
| 1S | 100 | 1 | 100 | 100 | 11.3 |
| 1T | 100 | 1 | 96.5 | 79.4 | 13.3 |
| 1U | 100 | 1 | 0 | 16.8 | 0.8 |
| 1V | 100 | 1 | 0 | 11.4 | 0.8 |
| Control | — | — | 0 | 0 | 0 |

TABLE 4

| Compound | Dose (mg/kg) | Number of doses | Cure rate (%) Day-4 | Cure rate (%) Day-6 | Days of survival (days) |
|---|---|---|---|---|---|
| 1a | 100 | 1 | 100 | 99 | 14.3 |
| 1b | 100 | 1 | 100 | 96 | 12.3 |
| 1c | 100 | 1 | 100 | 99 | 13.0 |
| Oxazin 170 perchlorate | 100 | 1 | 40 | 57 | 1.3 |
| Nile blue A | 100 | 1 | 15 | 5 | 0.3 |
| Nile red | 100 | 1 | 16 | 3 | 0 |

As is evident from Table 2, when the compound of the present invention was orally administered to the mice infected with malaria, high cure rates were observed and the days of survival were longer compared to the control in the cases of administration of 1A and 1B in amounts of 100 mg/kg and 30 mg/kg, and especially, in 1B, the complete cure was observed. On the other hand, with the known benzo[a]

phenoxazine compounds 1U and 1V (Non-patent Document 2) shown below, the effectiveness was hardly observed. Further, even with single oral administration of 1B in an amount of 300 mg/kg, abnormality in organs or death was not observed, demonstrating that it is excellent in safety. Also with hydrochloric acid salt of 1B, a similar effect was observed. Further, 1R,1S and 1T having a methyl group and a methanesulfonamidylethyl group on the A ring showed excellent cure effects in the in vivo tests using mice.

Further, as is evident from Table 3, novel benzo[a]phenoxazines (1a, 1b and 1c) showed high effectiveness in the in vivo tests using rodent malaria. However, Oxazin 170 perchlorate (Non-patent Document 6), Nile blue A (Non-patent Document 7) and Nile red which are known compounds did not show effectiveness.

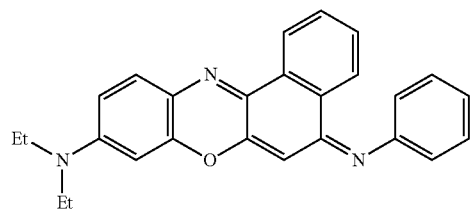

1U

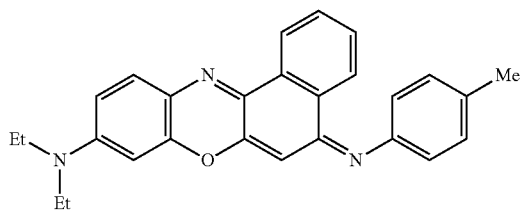

1V

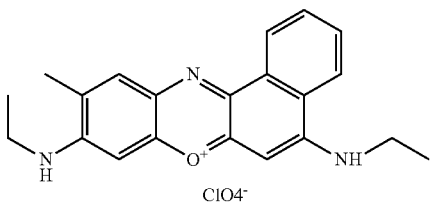

Oxazin 170 perchlorate

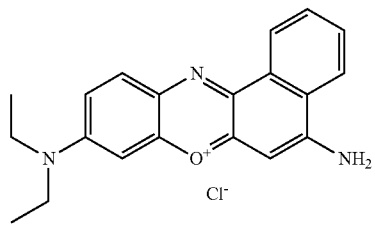

Nile blue A

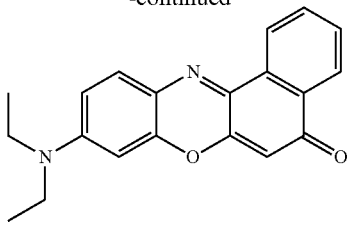

Nile red

[In Vitro Inhibition/Suppression Activities to African *Trypanosoma* Parasites, American *Trypanosoma* Parasites and *Leishmania* Parasites (In Vitro)]

1. Culture of African *Trypanosoma* Protozoa

In the present experiment, protozoa of Tripanosoma brucei rhodensiense (STIB 900 Strain), a trypomastigote living in blood stream, was used. The medium used in the experiment was a MEM medium which was sterilized with a filter and supplemented with 25 mM N-2-hydroxyeihylpiperazine-2-ethansulfonic acid (HEPES), 1 g/L glucose, 1% MEM non-essential amino acid, 0.2 mM 2-mercaptoethanol, 2 mM sodium pyruvate, 0.1 mM hypoxanthine, and 15% heat-treated horse serum. The protozoa was cultured in an atmosphere of $CO_2$ concentration 5%, at a temperature of 37° C.

2. African Trypanosome Protozoa Growth Inhibition Screening Test

The compounds of the present invention to be used in the present test and the positive control drug (melarsoprol) were dissolved in dimethylsulfoxide (DMSO) to make a test solution of a predetermined concentration.

A medium containing $8 \times 10^3$ protozoa, and a test solution containing a drug of a predetermined concentration of a drug-free DMSO were added to wells of a 96-well culture plate, and subsequently, medium was added so that the amount in each well becomes 100 µL. Test solutions were taken by duplicates.

After culturing the culture plate for 72 hours in an incubator, growth inhibition activity was tested. Test was conducted as follows. 10 µL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, to calculate the trypanosome protozoa infected rate of the test solution added-group, and of the control group.

3. Culture of American *Trypanosoma* Protozoa

In the present experiment, amastigote and trypomastigote infected with rat L6 cells of protozoa of *Trypanosoma cruzi* (Tulahuen C2C4 starin) were used. As medium used in the test, RPMI 1640 medium containing L6 cells was supplemented so that L-glutamine (200 mM) become 1%, fetal bovine serum becomes 10%, which was cultured under $CO_2$ concentration 5%, at 37° C.

4. American Trypanosome Protozoa Growth Inhibition Screening Test

The compounds of the present invention to be used in the present test and the positive control drug (benznidazole) were dissolved in DMSO to make a test solution of a predetermined concentration.

A medium containing $5 \times 10^3$ protozoa was added to wells of a 96-well culture plate, and pre-cultured for 48 hours. After replacing the medium, test solution containing drug of a predetermined concentration or a drug-free DMSO was added. Test solutions were taken by duplicates.

After culturing the culture plate in an incubator for 96 hours, growth inhibition activity was tested. Test was conducted as follows. 50 μL of CPRG/Nonidet was added to each well, and allowed to rest for 2 to 6 hours. Next, the culture plate was placed on a fluorescent micro-plate reader. The absorbance was measured at 540 nm, and the trypanosome infection rate of the test solution added group and control group were calculated.

5. Culture of Leishmaniasis Protozoa

In the present experiment, *Leishmania donovani* (MHOM/ET/67/L82 strain) was used. Protozoa was subcultured in Syrian Golden hamster, from which an amastigote was obtained. In the experiment, SM medium supplemented with 10% heat-treated bovine fetal serum was used, which was adjusted to pH 5.4, and cultured in an atmosphere of 5% $CO_2$ concentration, at 37° C.

6. *Leishmania* Protozoa Growth Inhibition Screening Test

The compounds of the present invention to be used in the present test and the positive control drug (miltefosine) were dissolved in DMSO to make a test solution of a predetermined concentration.

After adding a medium containing a predetermined number of protozoa to wells of a 96-well culture'plate and pre-treating, concentration of the amastigote was measured with CASY cell analysis system (Scharfe, Germany). Then, test solution containing a drug of a predetermined concentration or a drug-free DMSO was added. Test solutions were taken by duplicates.

After culturing the culture plate for 72 hours in an incubator, growth inhibition activity was tested. Test was conducted as follows. 10 μL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, and infection rate of *leishmania* protozoa of the test solution added group and control was calculated.

Based on the infection rate of each protozoa cell obtained in the above, growth inhibition rate was calculated, to obtain a 50% growth inhibition concentration ($EC_{50}$).

Growth inhibition rate (%)={1−(b−a)/(c−a)}×100 a: early infection rate
b: infection rate when test solution was added
c: infection rate of the control The inhibition/suppression activities of the benzo[a]phenoxazine compounds of the present invention to African *trypanosoma* parasites (*Trypanosoma brucei rhodesiense*), American *trypanosoma* parasites (*Trypanosoma cruzi*) and *leishmania* parasites (*Leishmania donovani*) obtained by the above experiments are shown in Table 5 and Table 6 below. From these, it can be seen that the benzo[a]phenoxazine compounds of the present invention significantly inhibit the growth of these protozoans.

TABLE 5

| | 50% Growth inhibition concentration (μg/ml) | | |
|---|---|---|---|
| Compound | *Trypanosoma brucei* rhod. | *Trypanosoma cruzi* | *Leishmania donovani* |
| 1A | 0.87 | 1.29 | 0.378 |
| 1B | 14.2 | 4.44 | 2.56 |
| 1F | 56.5 | >30 | 4.76 |

TABLE 5-continued

| | 50% Growth inhibition concentration (μg/ml) | | |
|---|---|---|---|
| Compound | *Trypanosoma brucei* rhod. | *Trypanosoma cruzi* | *Leishmania donovani* |
| 1G | 61 | >30 | 19.13 |
| 1H | 4.6 | 3.31 | 1.25 |
| 1I | 44.8 | >30 | 19.62 |
| 1J | 11.8 | 21.84 | 1.86 |
| 1K | 38.6 | >30 | 8.13 |
| 1L | 0.804 | 1.78 | 0.662 |
| 1M | 40 | >30 | 13.8 |
| Melarsoprol | 0.0024 | | |
| Benznidazole | | 0.2253 | |
| Milfotesine | | | 0.1135 |

TABLE 6

| Compound | *Trypanosoma brucei* rhod. | *Trypanosoma cruzi* | *Leishmania donovani* |
|---|---|---|---|
| 1R | 5.345 | 2.01 | 3.92 |
| 1S | 0.714 | 0.376 | 2.09 |
| 1a | 0.569 | 0.366 | 0.386 |
| 1b | 6.65 | 1.67 | 1.82 |
| 1c | 4.26 | 1.19 | 3.59 |

Industrial Applicability

By inclusion of a compound of the present invention as an active ingredient, an excellent therapeutic agent and/or prophylactic agent for a protozoal disease can be provided.

The invention claimed is:

1. A compound represented by any one of the following Structural Formulae 1B to 1H, 1J to 1M, 1P, 1R to 1T, and 1a to 1h, or a salt thereof:

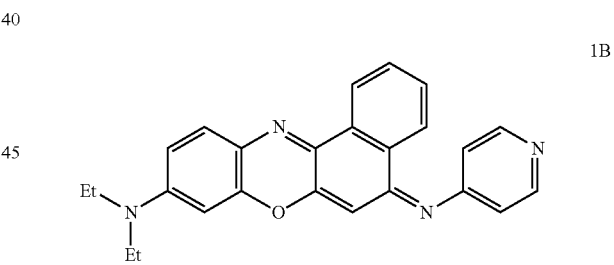

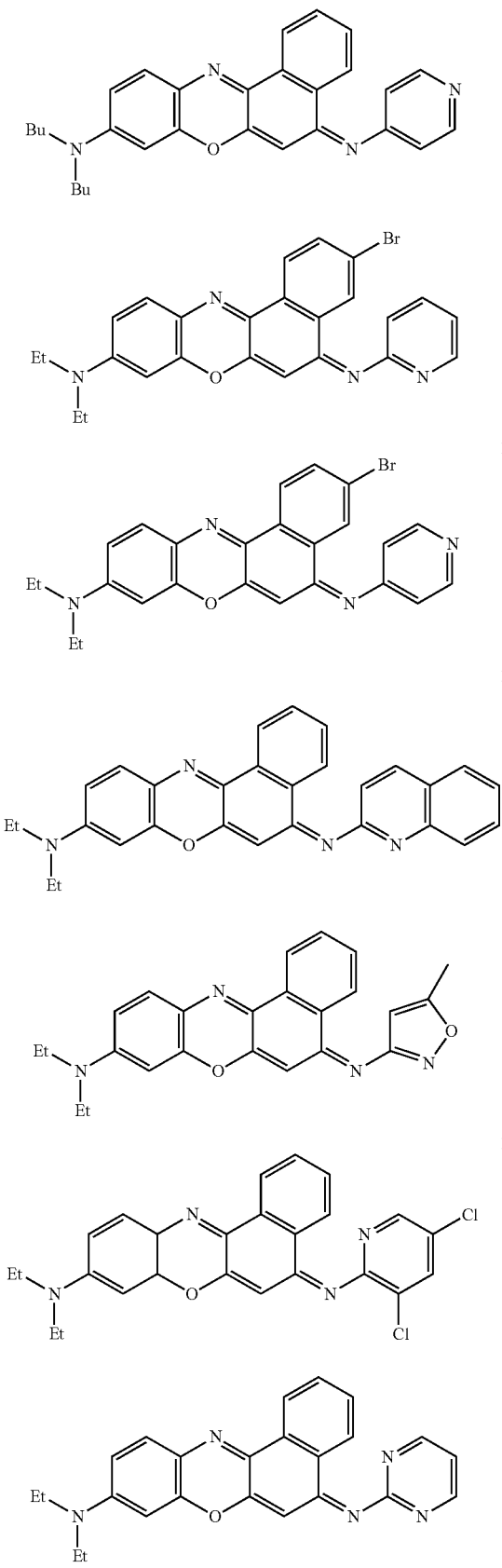
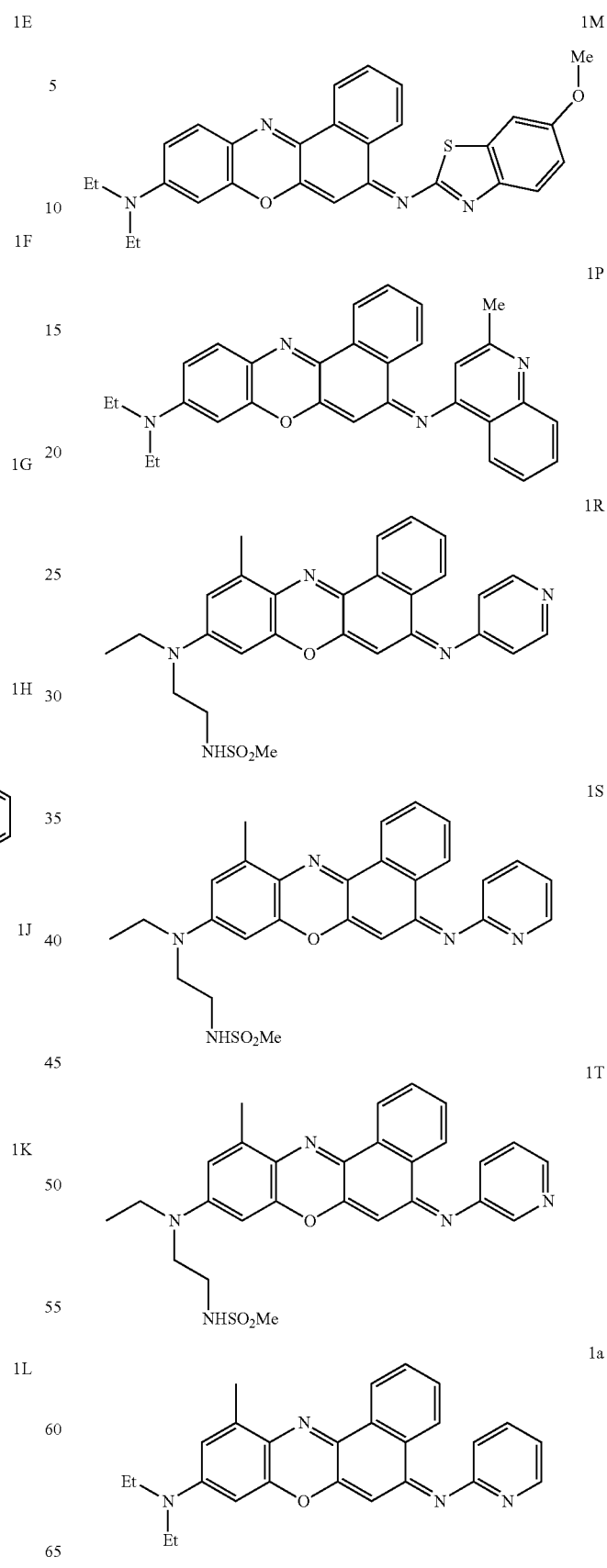

-continued

1b
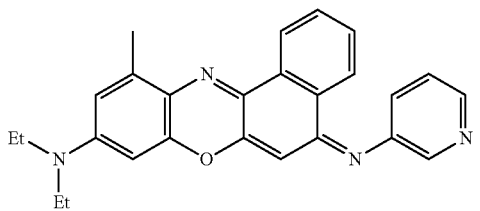

1c
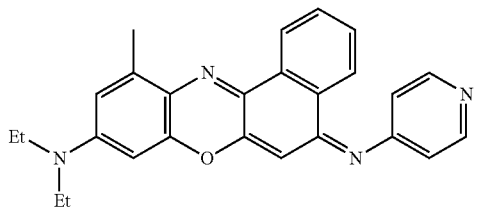

1d
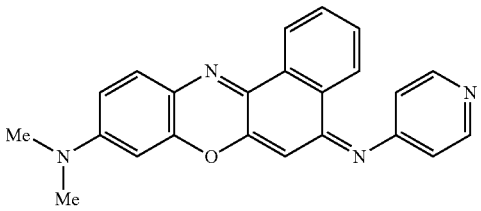

1e
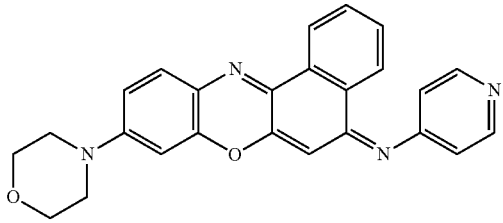

1f
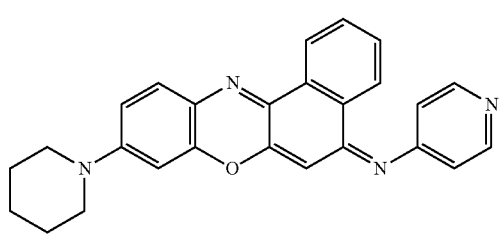

1g
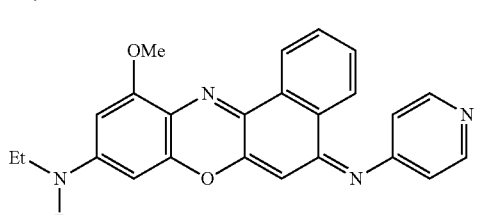

1h
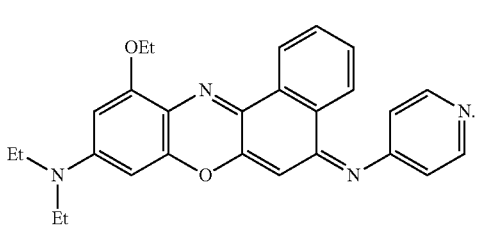

2. The compound or salt according to claim 1, wherein the compound or salt is a compound represented by Structural Formula 1B or a salt thereof.

3. A pharmaceutical composition comprising, as an active ingredient, the compound or salt according to claim 1 and a pharmaceutically acceptable carrier.

4. The pharmaceutical composition according to claim 3, further comprising chloroquine, mefloquine, artemisinin, atavaquone, pyrimethamine, suramin, pentamidine, melarsoprol, ascofuranone, beznidazole, pentostam, Amphotericin B, miltefosine, or fluconazole.

5. The pharmaceutical composition according to claim 3, further comprising a diluent.

6. The pharmaceutical composition according to claim 3, wherein the content of the active ingredient in the pharmaceutical composition is from 1 mg to 10,000 mg.

7. The pharmaceutical composition according to claim 3, wherein the content of the active ingredient in the pharmaceutical composition is from 10 mg to 3,000 mg.

8. The pharmaceutical composition according to claim 3, wherein the pharmaceutical composition is in the form of a liquid, tablet, or colloid.

9. A method of treating a protozoal disease, the method comprising administering, to a patient in need of treatment, a pharmaceutical composition that includes, as an active ingredient, the compound or salt according to claim 1 and a pharmaceutically acceptable carrier.

10. The method of treating a protozoal disease according to claim 9, wherein the active ingredient is represented by the following structural formula 1B:

1B

11. The method of treating a protozoal disease according to claim 9, wherein the protozoal disease is malariosis, leishmaniasis, African sleeping sickness, Chagas disease, toxoplasmosis, lymphatic filariasis, babesiosis or coccidiosis.

12. The method of treating a protozoal disease according to claim 9, wherein the protozoal disease is malariosis, leishmaniasis, African sleeping sickness, or Chagas disease.

13. The method of treating a protozoal disease according to claim 9, wherein the pharmaceutical composition further comprises chloroquine, mefloquine, artemisinin, atavaquone, pyrimethamine, suramin, pentamidine, melarsoprol, ascofuranone, beznidazole, pentostam, Amphotericin B, miltefosine, or fluconazole.

14. The method of treating a protozoal disease according to claim 9, wherein the pharmaceutical composition further comprises a diluent.

15. The method of treating a protozoal disease according to claim 9, wherein the content of the active ingredient in the pharmaceutical composition is from 1 mg to 10,000 mg.

16. The method of treating a protozoal disease according to claim 9, wherein the content of the active ingredient in the pharmaceutical composition is from 10 mg to 3,000 mg.

17. The method of treating a protozoal disease according to claim 9, wherein the pharmaceutical composition is in the form of a liquid, tablet, or colloid.

* * * * *